US012580086B2

(12) United States Patent
Bourke-Borrowes et al.

(10) Patent No.: US 12,580,086 B2
(45) Date of Patent: Mar. 17, 2026

(54) SYSTEM AND METHOD FOR EVALUATING THE LEVEL OF HARASSMENT OF INSECTS ON A PLURALITY OF ANIMALS

(71) Applicant: S.C.R. (ENGINEERS) LIMITED, Netanya (IL)

(72) Inventors: Hubert Bourke-Borrowes, Dublin (IE); Ratti Matteo, Piacenza (IT); Rotem Rabinovitz, Netanya (IL); Amit Sharir, Netanya (IL); Yuval Rapaport-Rom, Netanya (IL); Eran Genzel, Netanya (IL); Eden Weinberg, Netanya (IL); Oded Satat, Netanya (IL); Gilad Faktor, Netanya (IL); Doron Bar, Netanya (IL); Hagen Wille, Netanya (IL)

(73) Assignee: S.C.R. (ENGINEERS) LIMITED, Netanya (IL)

( * ) Notice: Subject to any disclaimer, the term of this patent is extended or adjusted under 35 U.S.C. 154(b) by 0 days.

(21) Appl. No.: 18/263,539

(22) PCT Filed: Feb. 8, 2022

(86) PCT No.: PCT/IL2022/050161
§ 371 (c)(1),
(2) Date: Jul. 31, 2023

(87) PCT Pub. No.: WO2022/172266
PCT Pub. Date: Aug. 18, 2022

(65) Prior Publication Data
US 2024/0363257 A1     Oct. 31, 2024

(30) Foreign Application Priority Data
Feb. 9, 2021    (IL) ......................................... 280744

(51) Int. Cl.
*G16H 50/80* (2018.01)
*A01K 29/00* (2006.01)
(Continued)

(52) U.S. Cl.
CPC ........... *G16H 50/80* (2018.01); *A01K 29/005* (2013.01); *G16H 40/63* (2018.01); *G16H 50/70* (2018.01)

(58) Field of Classification Search
None
See application file for complete search history.

(56) References Cited

U.S. PATENT DOCUMENTS 85,575 A    1/1869  Drake
377,588 A   2/1888  Walsh, Jr.
(Continued)

FOREIGN PATENT DOCUMENTS

AU      199534570    10/1994
AU      2003239832    5/2002
(Continued)

OTHER PUBLICATIONS

Opio C., Gerber, P., Mottet, A., Falcucci, A., Tempio, G., Macleod, M., Vellinga, T., Henderson, B. & Steinfeld, H.: "Greenhouse gas emissions from ruminant supply chains", A Global Life Cycle. Assessment, Jan. 1, 2013 (Jan. 1, 2013), pp. 1-214, XP093010534.
(Continued)

*Primary Examiner* — Magdalena Topolski
(74) *Attorney, Agent, or Firm* — S.J. INTELLECTUAL PROPERTY LTD.

(57) ABSTRACT

The presently disclosed subject matter aims to a system and method for evaluating the level of harassment of flying insects on a plurality of animals located at a given area, the system comprising a processing circuitry configured to: obtain one or more ear movement patterns associated with at
(Continued)

least one ear of at least one animal of the plurality of animals, each ear movement pattern is associated with respective ear movement characteristics; for at least part of the one or more ear movement patterns, determine whether their respective ear movement characteristics meet a predefined rule; and, determine whether a number of ear movement patterns whose ear movement characteristics met the predefined rule meets an action requirement rule.

16 Claims, 13 Drawing Sheets

(51) Int. Cl.
    *G16H 40/63*        (2018.01)
    *G16H 50/70*        (2018.01)

(56)             References Cited

U.S. PATENT DOCUMENTS

| | | |
|---|---|---|
| 584,121 A | 6/1897 | Sanders |
| 818,783 A | 4/1906 | Philippi |
| 823,079 A | 6/1906 | Rais |
| 1,016,752 A | 2/1912 | Leith |
| 1,188,510 A | 6/1916 | Timson |
| 1,364,137 A | 1/1921 | Pannier |
| 1,759,400 A | 5/1930 | Hobbs |
| 1,843,314 A | 2/1932 | Berntson et al. |
| 1,863,037 A | 6/1932 | Archbold |
| 2,078,827 A | 4/1937 | Ketchum |
| 2,420,020 A | 5/1947 | Snell |
| 2,553,400 A | 5/1951 | Blair |
| 2,570,048 A | 10/1951 | Cooke et al. |
| 3,091,770 A | 6/1963 | Mcmurray et al. |
| 3,261,243 A | 7/1966 | Ellison |
| 3,596,541 A | 8/1971 | Bieganski |
| 3,812,859 A | 5/1974 | Murphy et al. |
| 3,884,100 A | 5/1975 | Fideldy |
| 3,981,209 A | 9/1976 | Caroff |
| 4,120,303 A | 10/1978 | Villa-Massone et al. |
| 4,121,591 A | 10/1978 | Hayes |
| 4,281,657 A | 8/1981 | Ritchey |
| 4,323,183 A | 4/1982 | Duchin |
| 4,497,321 A | 2/1985 | Fearing et al. |
| 4,516,577 A | 5/1985 | Scott et al. |
| 4,531,520 A | 7/1985 | Reggers et al. |
| 4,552,147 A | 11/1985 | Gardner |
| 4,666,436 A | 5/1987 | McDonald et al. |
| 4,672,966 A | 6/1987 | Haas, Jr. |
| 4,696,119 A | 9/1987 | Howe et al. |
| 4,716,899 A | 1/1988 | Huenefeld et al. |
| 4,819,639 A | 4/1989 | Gardner |
| 4,821,683 A | 4/1989 | Veldman |
| 4,878,302 A | 11/1989 | Jowsey |
| 4,943,294 A | 7/1990 | Knapp |
| 5,022,253 A | 6/1991 | Parlatore |
| 5,056,385 A | 10/1991 | Petersen |
| 5,141,514 A | 8/1992 | van Amelsfort |
| 5,154,721 A | 10/1992 | Perez |
| 5,267,464 A | 12/1993 | Cleland |
| 5,509,291 A | 4/1996 | Nilsson et al. |
| 5,651,791 A | 7/1997 | Zavlodaver et al. |
| 5,778,820 A | 7/1998 | van der Lely et al. |
| 6,007,548 A | 12/1999 | Ritchey |
| 6,016,769 A | 1/2000 | Forster |
| 6,043,748 A | 3/2000 | Touchton et al. |
| 6,053,926 A | 4/2000 | Luehrs |
| 6,095,915 A | 8/2000 | Battista et al. |
| 6,099,482 A | 8/2000 | Brune et al. |
| 6,100,804 A | 8/2000 | Brady et al. |
| 6,113,539 A | 9/2000 | Ridenour |
| 6,114,957 A | 9/2000 | Westrick et al. |
| 6,145,225 A | 11/2000 | Ritchey |
| 6,166,643 A | 12/2000 | Janning et al. |

| | | |
|---|---|---|
| 6,172,640 B1 | 1/2001 | Durst et al. |
| 6,232,880 B1 | 5/2001 | Anderson et al. |
| 6,235,036 B1 | 5/2001 | Gardner et al. |
| 6,271,757 B1 | 8/2001 | Touchton et al. |
| 6,297,739 B1 | 10/2001 | Small |
| 6,310,553 B1 | 10/2001 | Dance |
| 6,402,692 B1 | 6/2002 | Morford |
| 6,497,197 B1 | 12/2002 | Huisma |
| 6,502,060 B1 | 12/2002 | Christian |
| 6,510,630 B1 | 1/2003 | Gardner |
| 6,535,131 B1 | 3/2003 | Bar-Shalom et al. |
| 6,569,092 B1 | 5/2003 | Guichon et al. |
| 6,659,039 B1 | 12/2003 | Larsen |
| 6,772,556 B1 | 8/2004 | Liu |
| 6,868,804 B1 | 3/2005 | Huisma et al. |
| 7,016,730 B2 | 3/2006 | Ternes |
| 7,046,152 B1 | 5/2006 | Peinetti et al. |
| 7,137,359 B1 | 11/2006 | Braden |
| 7,296,539 B2 | 11/2007 | Iljas |
| 7,380,518 B2 | 6/2008 | Kates |
| 7,705,736 B1 | 4/2010 | Kedziora |
| 7,772,979 B2 | 8/2010 | Nehls |
| 7,843,350 B2 | 11/2010 | Geissler et al. |
| 7,937,861 B1 | 5/2011 | Zacher |
| 8,005,624 B1 | 8/2011 | Starr |
| 8,266,990 B1 | 9/2012 | Janson |
| 8,305,220 B2 | 11/2012 | Gibson |
| 8,478,389 B1 | 7/2013 | Brockway et al. |
| 8,622,929 B2 | 1/2014 | Wilson et al. |
| 8,763,557 B2 | 7/2014 | Lipscomb et al. |
| 8,955,462 B1 | 2/2015 | Golden et al. |
| 8,979,757 B2 | 3/2015 | Mottram et al. |
| 9,215,862 B2 | 12/2015 | Bladen et al. |
| 9,392,767 B2 | 7/2016 | Johnson, III et al. |
| 9,392,946 B1 | 7/2016 | Sarantos et al. |
| 9,449,487 B1 | 9/2016 | Spitalny |
| 9,648,849 B1 | 5/2017 | Vivathana |
| 9,654,925 B1 | 5/2017 | Solinsky et al. |
| 9,693,536 B1 | 7/2017 | Dana |
| 9,717,216 B1 | 8/2017 | Schlachta et al. |
| 9,743,643 B1 | 8/2017 | Kaplan et al. |
| 9,848,577 B1 | 12/2017 | Brandao et al. |
| 9,861,080 B1 | 1/2018 | Hathway et al. |
| 10,004,204 B2 | 6/2018 | Hayes et al. |
| 10,021,857 B2 | 7/2018 | Bailey et al. |
| 10,039,263 B2 | 8/2018 | Teychene et al. |
| 10,045,511 B1 | 8/2018 | Yarden et al. |
| 10,064,391 B1 | 9/2018 | Riley |
| 10,091,972 B1 | 10/2018 | Jensen et al. |
| 10,231,442 B1 | 3/2019 | Chang et al. |
| 10,242,547 B1 | 3/2019 | Struhsaker |
| 10,264,762 B1 | 4/2019 | Lamb |
| 10,352,759 B1 | 7/2019 | Jensen |
| 10,354,342 B2 | 7/2019 | Kuper et al. |
| 10,446,006 B1 | 10/2019 | Johnson, Jr. et al. |
| 10,512,430 B1 | 12/2019 | Hladio |
| 10,537,654 B2 | 1/2020 | Becker |
| 10,588,295 B1 | 3/2020 | Riley |
| 10,628,756 B1 | 4/2020 | Kuper et al. |
| 10,638,726 B1 | 5/2020 | Makarychev et al. |
| 10,691,674 B2 | 6/2020 | Leong et al. |
| 11,980,526 B2 * | 5/2024 | Brandao ............. A01K 13/003 |
| 12,239,113 B2 * | 3/2025 | Hicks ...................... A01K 7/02 |
| 2001/0027751 A1 | 10/2001 | van den Berg |
| 2002/0010390 A1 | 1/2002 | Guice et al. |
| 2002/0021219 A1 | 2/2002 | Edwards |
| 2002/0091326 A1 | 7/2002 | Hashimoto et al. |
| 2002/0095828 A1 | 7/2002 | Koopman et al. |
| 2002/0154015 A1 | 10/2002 | Hixson |
| 2002/0158765 A1 | 10/2002 | Pape et al. |
| 2003/0004652 A1 | 1/2003 | Brunner et al. |
| 2003/0023517 A1 | 1/2003 | Marsh et al. |
| 2003/0028327 A1 | 2/2003 | Brunner et al. |
| 2003/0062001 A1 | 4/2003 | Andersson |
| 2003/0066491 A1 | 4/2003 | Stampe |
| 2003/0144926 A1 | 7/2003 | Bodin et al. |
| 2003/0146284 A1 | 8/2003 | Schmit et al. |
| 2003/0149526 A1 | 8/2003 | Zhou et al. |
| 2003/0177025 A1 | 9/2003 | Curkendall et al. |

(56)　　　　　References Cited

U.S. PATENT DOCUMENTS

| | | |
|---|---|---|
| 2003/0201931 A1 | 10/2003 | Durst et al. |
| 2003/0208157 A1 | 11/2003 | Eidson et al. |
| 2003/0221343 A1 | 12/2003 | Volk et al. |
| 2003/0229452 A1 | 12/2003 | Lewis et al. |
| 2004/0066298 A1 | 4/2004 | Schmitt et al. |
| 2004/0078390 A1 | 4/2004 | Saunders |
| 2004/0118920 A1 | 6/2004 | He |
| 2004/0123810 A1 | 7/2004 | Lorton et al. |
| 2004/0177011 A1 | 9/2004 | Ramsay et al. |
| 2004/0201454 A1 | 10/2004 | Waterhouse et al. |
| 2005/0010333 A1 | 1/2005 | Lorton et al. |
| 2005/0026181 A1 | 2/2005 | Davis et al. |
| 2005/0097997 A1 | 5/2005 | Hile |
| 2005/0108912 A1 | 5/2005 | Bekker |
| 2005/0115508 A1 | 6/2005 | Little |
| 2005/0128086 A1 | 6/2005 | Brown et al. |
| 2005/0139168 A1 | 6/2005 | Light et al. |
| 2005/0145187 A1 | 7/2005 | Gray |
| 2005/0273117 A1 | 12/2005 | Teychene |
| 2005/0279287 A1 | 12/2005 | Kroeker |
| 2005/0284381 A1 | 12/2005 | Bell et al. |
| 2006/0011145 A1 | 1/2006 | Kates |
| 2006/0052986 A1 | 3/2006 | Rogers et al. |
| 2006/0064325 A1 | 3/2006 | Matsumoto et al. |
| 2006/0087440 A1 | 4/2006 | Klein |
| 2006/0106289 A1 | 5/2006 | Elser |
| 2006/0117619 A1 | 6/2006 | Costantini |
| 2006/0155172 A1 | 7/2006 | Rugg |
| 2006/0170561 A1 | 8/2006 | Eyal |
| 2006/0173367 A1 | 8/2006 | Stuart et al. |
| 2006/0185605 A1 | 8/2006 | Renz et al. |
| 2006/0201436 A1 | 9/2006 | Kates |
| 2006/0207515 A1 | 9/2006 | Palett et al. |
| 2006/0241521 A1 | 10/2006 | Cohen |
| 2006/0282274 A1 | 12/2006 | Bennett |
| 2006/0290514 A1 | 12/2006 | Sakama et al. |
| 2007/0006494 A1 | 1/2007 | Hayes et al. |
| 2007/0008155 A1 | 1/2007 | Trost et al. |
| 2007/0021660 A1 | 1/2007 | Delonzor et al. |
| 2007/0027375 A1 | 2/2007 | Melker et al. |
| 2007/0027377 A1 | 2/2007 | Delonzor et al. |
| 2007/0027379 A1 | 2/2007 | Delonzor et al. |
| 2007/0029381 A1 | 2/2007 | Braiman |
| 2007/0044317 A1 | 3/2007 | Critelli |
| 2007/0044732 A1 | 3/2007 | Araki et al. |
| 2007/0062457 A1 | 3/2007 | Bates et al. |
| 2007/0069899 A1 | 3/2007 | Shih et al. |
| 2007/0103296 A1 | 5/2007 | Paessel et al. |
| 2007/0149871 A1 | 6/2007 | Sarussi et al. |
| 2007/0152825 A1 | 7/2007 | August et al. |
| 2007/0222624 A1 | 9/2007 | Eicken et al. |
| 2007/0255124 A1 | 11/2007 | Pologe et al. |
| 2007/0258625 A1 | 11/2007 | Mirtsching |
| 2007/0283791 A1 | 12/2007 | Engvall et al. |
| 2007/0298421 A1 | 12/2007 | Jiang et al. |
| 2008/0001815 A1 | 1/2008 | Wang et al. |
| 2008/0004798 A1 | 1/2008 | Troxler et al. |
| 2008/0017126 A1 | 1/2008 | Adams et al. |
| 2008/0018481 A1 | 1/2008 | Zehavi |
| 2008/0021352 A1 | 1/2008 | Keegan et al. |
| 2008/0036610 A1 | 2/2008 | Hokuf et al. |
| 2008/0047177 A1 | 2/2008 | Hilpert |
| 2008/0055155 A1 | 3/2008 | Hensley et al. |
| 2008/0059263 A1 | 3/2008 | Stroman et al. |
| 2008/0061990 A1 | 3/2008 | Milnes et al. |
| 2008/0076988 A1 | 3/2008 | Sarussi et al. |
| 2008/0076992 A1 | 3/2008 | Hete et al. |
| 2008/0085522 A1 | 4/2008 | Meghen et al. |
| 2008/0097726 A1 | 4/2008 | Lorton et al. |
| 2008/0110406 A1 | 5/2008 | Anderson et al. |
| 2008/0146890 A1 | 6/2008 | LeBoeuf et al. |
| 2008/0173255 A1 | 7/2008 | Mainini et al. |
| 2008/0190202 A1 | 8/2008 | Kulach et al. |
| 2008/0190379 A1 | 8/2008 | Mainini et al. |
| 2008/0215484 A1 | 9/2008 | Oldham |
| 2008/0227662 A1 | 9/2008 | Stromberg et al. |
| 2008/0228105 A1 | 9/2008 | Howell et al. |
| 2008/0262326 A1 | 10/2008 | Hete et al. |
| 2008/0272908 A1 | 11/2008 | Boyd |
| 2008/0312511 A1 | 12/2008 | Osler et al. |
| 2009/0009388 A1 | 1/2009 | Wangrud |
| 2009/0020613 A1 | 1/2009 | Chang et al. |
| 2009/0025651 A1 | 1/2009 | Lalor |
| 2009/0058730 A1 | 3/2009 | Geissler et al. |
| 2009/0094869 A1 | 4/2009 | Geissler et al. |
| 2009/0102668 A1 | 4/2009 | Thompson et al. |
| 2009/0139462 A1 | 6/2009 | So |
| 2009/0149727 A1 | 6/2009 | Truitt et al. |
| 2009/0187392 A1 | 7/2009 | Riskey et al. |
| 2009/0255484 A1 | 10/2009 | Muelken |
| 2009/0312667 A1 | 12/2009 | Utsunomiya et al. |
| 2010/0018363 A1 | 1/2010 | Chervenak et al. |
| 2010/0030036 A1 | 2/2010 | Mottram et al. |
| 2010/0113902 A1 | 5/2010 | Hete et al. |
| 2010/0139575 A1 | 6/2010 | Duncan et al. |
| 2010/0160809 A1 | 6/2010 | Laurence et al. |
| 2010/0175625 A1 | 7/2010 | Klenotiz et al. |
| 2010/0217102 A1 | 8/2010 | LeBoeuf et al. |
| 2010/0250198 A1 | 9/2010 | Lorton et al. |
| 2010/0289639 A1 | 11/2010 | Gibson et al. |
| 2010/0315241 A1 | 12/2010 | Jow |
| 2010/0321182 A1 | 12/2010 | Wangrud |
| 2010/0321189 A1 | 12/2010 | Gibson et al. |
| 2010/0331739 A1 | 12/2010 | Maltz et al. |
| 2011/0018717 A1 | 1/2011 | Takahashi et al. |
| 2011/0041367 A1 | 2/2011 | Bladen et al. |
| 2011/0061605 A1 | 3/2011 | Hardi et al. |
| 2011/0095089 A1 | 4/2011 | Kolton et al. |
| 2011/0121356 A1 | 5/2011 | Krawinkel et al. |
| 2011/0137185 A1 | 6/2011 | Hete et al. |
| 2011/0152876 A1 | 6/2011 | Vandeputte |
| 2011/0178423 A1 | 7/2011 | Hatch |
| 2011/0192213 A1 | 8/2011 | Zimmerman |
| 2011/0203144 A1 | 8/2011 | Junek et al. |
| 2011/0258130 A1 | 10/2011 | Grabiner et al. |
| 2011/0272470 A1 | 11/2011 | Baba et al. |
| 2011/0313264 A1 | 12/2011 | Hete |
| 2012/0009943 A1 | 1/2012 | Greenberg et al. |
| 2012/0068848 A1 | 3/2012 | Campbell et al. |
| 2012/0089152 A1 | 4/2012 | Lynd et al. |
| 2012/0092132 A1 | 4/2012 | Holme et al. |
| 2012/0111286 A1 | 5/2012 | Lee et al. |
| 2012/0112917 A1 | 5/2012 | Menachem et al. |
| 2012/0160181 A1 | 6/2012 | So et al. |
| 2012/0175412 A1 | 7/2012 | Grabiner et al. |
| 2012/0204811 A1 | 8/2012 | Ryan |
| 2012/0236690 A1 | 9/2012 | Rader et al. |
| 2012/0291715 A1 | 11/2012 | Jiang et al. |
| 2012/0299731 A1 | 11/2012 | Triener |
| 2012/0325153 A1 | 12/2012 | Mostert |
| 2012/0326862 A1 | 12/2012 | Kwak et al. |
| 2012/0326874 A1 | 12/2012 | Kwak et al. |
| 2013/0006065 A1 | 1/2013 | Yanai et al. |
| 2013/0014706 A1 | 1/2013 | Menkes |
| 2013/0046170 A1 | 2/2013 | Haynes et al. |
| 2013/0113622 A1 | 5/2013 | Pratt et al. |
| 2013/0119142 A1 | 5/2013 | McCoy et al. |
| 2013/0175347 A1 | 7/2013 | Decaluwe et al. |
| 2013/0192526 A1 | 8/2013 | Mainini |
| 2013/0211773 A1 | 8/2013 | Loeschinger et al. |
| 2013/0222141 A1 | 8/2013 | Rhee et al. |
| 2013/0237778 A1 | 9/2013 | Rouquette et al. |
| 2013/0239904 A1 | 9/2013 | Kim et al. |
| 2013/0239907 A1 | 9/2013 | Laurence et al. |
| 2013/0265165 A1 | 10/2013 | So et al. |
| 2013/0282295 A1 | 10/2013 | White et al. |
| 2013/0285815 A1 | 10/2013 | Jones, II |
| 2014/0073486 A1 | 3/2014 | Ahmed et al. |
| 2014/0122488 A1 | 5/2014 | Jung et al. |
| 2014/0123912 A1 | 5/2014 | Menkes et al. |
| 2014/0135596 A1 | 5/2014 | LeBoeuf et al. |
| 2014/0135631 A1 | 5/2014 | Brumback et al. |
| 2014/0171762 A1 | 6/2014 | LeBoeuf et al. |
| 2014/0174376 A1 | 6/2014 | Touchton et al. |

(56) References Cited

U.S. PATENT DOCUMENTS

| | | |
|---|---|---|
| 2014/0196673 A1 | 7/2014 | Menkes et al. |
| 2014/0230755 A1 | 8/2014 | Trenkle et al. |
| 2014/0232541 A1 | 8/2014 | Trenkle et al. |
| 2014/0253709 A1 | 9/2014 | Bresch et al. |
| 2014/0261235 A1 | 9/2014 | Rich et al. |
| 2014/0267299 A1 | 9/2014 | Couse |
| 2014/0275824 A1 | 9/2014 | Couse |
| 2014/0276089 A1 | 9/2014 | Kirenko et al. |
| 2014/0290013 A1 | 10/2014 | Eidelman et al. |
| 2014/0302783 A1 | 10/2014 | Aiuto et al. |
| 2014/0331942 A1 | 11/2014 | Sarazyn |
| 2014/0333439 A1 | 11/2014 | Downing et al. |
| 2014/0347184 A1 | 11/2014 | Triener |
| 2014/0352632 A1 | 12/2014 | Mclaughlin |
| 2014/0368338 A1 | 12/2014 | Rettedal et al. |
| 2015/0025394 A1 | 1/2015 | Hong et al. |
| 2015/0057963 A1 | 2/2015 | Zakharov et al. |
| 2015/0097668 A1 | 4/2015 | Toth |
| 2015/0099472 A1 | 4/2015 | Ickovic |
| 2015/0100245 A1 | 4/2015 | Huang et al. |
| 2015/0107519 A1 | 4/2015 | Rajkondawar et al. |
| 2015/0107522 A1 | 4/2015 | Lamb |
| 2015/0109130 A1 | 4/2015 | Rajkondawar et al. |
| 2015/0122893 A1 | 5/2015 | Warther |
| 2015/0128873 A1 | 5/2015 | Prescott et al. |
| 2015/0130617 A1 | 5/2015 | Triener |
| 2015/0148811 A1 | 5/2015 | Swope et al. |
| 2015/0157435 A1 | 6/2015 | Chasins et al. |
| 2015/0182322 A1 | 7/2015 | Couse et al. |
| 2015/0245592 A1 | 9/2015 | Sibbald et al. |
| 2015/0282457 A1 | 10/2015 | Yarden |
| 2015/0334994 A1 | 11/2015 | Prasad |
| 2015/0342143 A1 | 12/2015 | Stewart |
| 2015/0351885 A1 | 12/2015 | Kool et al. |
| 2015/0366166 A1 | 12/2015 | Mueller |
| 2016/0000045 A1 | 1/2016 | Funaya et al. |
| 2016/0021506 A1 | 1/2016 | Bonge, Jr. |
| 2016/0058379 A1 | 3/2016 | Menkes et al. |
| 2016/0066546 A1 | 3/2016 | Borchersen et al. |
| 2016/0100802 A1 | 4/2016 | Newman |
| 2016/0106064 A1 | 4/2016 | Bladen et al. |
| 2016/0113524 A1 | 4/2016 | Gross et al. |
| 2016/0120154 A1 | 5/2016 | Hill et al. |
| 2016/0128637 A1 | 5/2016 | LeBoeuf et al. |
| 2016/0135431 A1 | 5/2016 | Siegel |
| 2016/0148086 A1 | 5/2016 | Clarke et al. |
| 2016/0150362 A1 | 5/2016 | Shaprio et al. |
| 2016/0151013 A1 | 6/2016 | Atallah et al. |
| 2016/0165851 A1 | 6/2016 | Harty et al. |
| 2016/0165852 A1 | 6/2016 | Goldfain |
| 2016/0166761 A1 | 6/2016 | Piehl et al. |
| 2016/0198957 A1 | 7/2016 | Arditi et al. |
| 2016/0210841 A1 | 7/2016 | Huang et al. |
| 2016/0278712 A1 | 9/2016 | Sagara et al. |
| 2016/0286757 A1 | 10/2016 | Armstrong |
| 2016/0287108 A1 | 10/2016 | Wei et al. |
| 2016/0317049 A1 | 11/2016 | LeBoeuf et al. |
| 2016/0324188 A1 | 11/2016 | Johnston et al. |
| 2016/0345881 A1 | 12/2016 | Sarantos et al. |
| 2016/0360733 A1 | 12/2016 | Triener |
| 2017/0000090 A1 | 1/2017 | Hall |
| 2017/0006826 A1* | 1/2017 | Torres .................. A01K 13/003 |
| 2017/0006836 A1 | 1/2017 | Torres |
| 2017/0042119 A1 | 2/2017 | Garrity |
| 2017/0067770 A1 | 3/2017 | Sun |
| 2017/0079247 A1 | 3/2017 | Womble et al. |
| 2017/0095206 A1 | 4/2017 | Leib et al. |
| 2017/0156288 A1 | 6/2017 | Singh |
| 2017/0164905 A1 | 6/2017 | Gumiero |
| 2017/0193208 A1 | 7/2017 | Ashley et al. |
| 2017/0196203 A1 | 7/2017 | Huisma et al. |
| 2017/0202185 A1 | 7/2017 | Trumbull et al. |
| 2017/0245797 A1 | 8/2017 | Quinn |
| 2017/0258039 A1 | 9/2017 | Lauterbach |
| 2017/0272842 A1 | 9/2017 | Touma |
| 2017/0280675 A1 | 10/2017 | MacNeil et al. |
| 2017/0280688 A1 | 10/2017 | Deliou et al. |
| 2017/0281822 A1 | 10/2017 | Becker |
| 2017/0318781 A1 | 11/2017 | Rollins et al. |
| 2017/0360004 A1 | 12/2017 | Carver |
| 2017/0372583 A1 | 12/2017 | Lamkin et al. |
| 2018/0000045 A1 | 1/2018 | Bianchi et al. |
| 2018/0007863 A1 | 1/2018 | Bailey et al. |
| 2018/0014512 A1 | 1/2018 | Arabani et al. |
| 2018/0027772 A1 | 2/2018 | Gordon et al. |
| 2018/0055016 A1 | 3/2018 | Hsieh et al. |
| 2018/0064068 A1 | 3/2018 | McKee et al. |
| 2018/0070559 A1 | 3/2018 | So |
| 2018/0098522 A1 | 4/2018 | Steinfort |
| 2018/0110205 A1 | 4/2018 | Czarnecky et al. |
| 2018/0113498 A1 | 4/2018 | Cronin et al. |
| 2018/0131074 A1 | 5/2018 | Wilkinson et al. |
| 2018/0132455 A1 | 5/2018 | Pradeep et al. |
| 2018/0146645 A1 | 5/2018 | Arbel |
| 2018/0206455 A1 | 7/2018 | Thiex et al. |
| 2018/0242860 A1 | 8/2018 | LeBoeuf et al. |
| 2018/0249683 A1 | 9/2018 | Borchersen et al. |
| 2018/0260976 A1 | 9/2018 | Watanabe et al. |
| 2018/0271058 A1 | 9/2018 | Valdez |
| 2018/0279582 A1 | 10/2018 | Yajima et al. |
| 2018/0288968 A1 | 10/2018 | Cisco et al. |
| 2018/0295809 A1 | 10/2018 | Yajima et al. |
| 2018/0303425 A1 | 10/2018 | Wordham et al. |
| 2018/0310526 A1 | 11/2018 | Birch et al. |
| 2018/0325382 A1 | 11/2018 | Brandao et al. |
| 2018/0332989 A1 | 11/2018 | Chiu et al. |
| 2018/0333244 A1 | 11/2018 | Hanks et al. |
| 2019/0008118 A1 | 1/2019 | Keegan |
| 2019/0008124 A1 | 1/2019 | Komatsu et al. |
| 2019/0029226 A1 | 1/2019 | Triener |
| 2019/0053469 A1 | 2/2019 | Mardirossian |
| 2019/0053470 A1 | 2/2019 | Singh et al. |
| 2019/0059335 A1 | 2/2019 | Crider, Jr. et al. |
| 2019/0059337 A1 | 2/2019 | Robbins |
| 2019/0059741 A1 | 2/2019 | Crider, Jr. et al. |
| 2019/0069512 A1 | 3/2019 | Eriksson et al. |
| 2019/0075945 A1 | 3/2019 | Strassburger et al. |
| 2019/0082654 A1 | 3/2019 | Robbins |
| 2019/0090754 A1 | 3/2019 | Brandao et al. |
| 2019/0110433 A1 | 4/2019 | Myers |
| 2019/0110436 A1 | 4/2019 | Gardner et al. |
| 2019/0125509 A1 | 5/2019 | Hotchkin |
| 2019/0130728 A1 | 5/2019 | Struhsaker et al. |
| 2019/0133086 A1 | 5/2019 | Katz et al. |
| 2019/0159428 A1 | 5/2019 | Bolen |
| 2019/0166802 A1 | 6/2019 | Seltzer et al. |
| 2019/0183091 A1 | 6/2019 | Betts-Lacroix et al. |
| 2019/0183092 A1 | 6/2019 | Couse et al. |
| 2019/0208358 A1 | 7/2019 | de Barros Chapiewski et al. |
| 2019/0213860 A1 | 7/2019 | Shaprio et al. |
| 2019/0254599 A1 | 8/2019 | Young et al. |
| 2019/0287429 A1 | 9/2019 | Dawson et al. |
| 2019/0290133 A1 | 9/2019 | Crider et al. |
| 2019/0290847 A1 | 9/2019 | Veyrent et al. |
| 2019/0298226 A1 | 10/2019 | Filipowicz |
| 2019/0298924 A1 | 10/2019 | Gibson et al. |
| 2019/0327939 A1 | 10/2019 | Sharpe et al. |
| 2019/0335715 A1 | 11/2019 | Hicks et al. |
| 2019/0350168 A1 | 11/2019 | Shi |
| 2019/0365324 A1 | 12/2019 | Chang |
| 2019/0373857 A1 | 12/2019 | Leigh-Lancaster et al. |
| 2019/0380311 A1 | 12/2019 | Crouthamel et al. |
| 2019/0385037 A1 | 12/2019 | Robadey et al. |
| 2019/0385332 A1 | 12/2019 | Yajima et al. |
| 2019/0387711 A1 | 12/2019 | Flennert et al. |
| 2020/0015740 A1 | 1/2020 | Alnofeli et al. |
| 2020/0037886 A1 | 2/2020 | Greer et al. |
| 2020/0068853 A1 | 3/2020 | Radovcic |
| 2020/0085019 A1 | 3/2020 | Gilbert et al. |
| 2020/0100463 A1 | 4/2020 | Rooda et al. |
| 2020/0107522 A1 | 4/2020 | Kersey et al. |
| 2020/0110946 A1 | 4/2020 | Kline et al. |
| 2020/0113728 A1 | 4/2020 | Spector et al. |
| 2020/0170222 A1 | 6/2020 | Gotts |

(56)            References Cited

U.S. PATENT DOCUMENTS

| | | |
|---|---|---|
| 2020/0178504 A1 | 6/2020 | Moss |
| 2020/0178505 A1 | 6/2020 | Womble et al. |
| 2020/0178800 A1 | 6/2020 | Geissler et al. |
| 2020/0205381 A1 | 7/2020 | Wernimont et al. |
| 2020/0229391 A1 | 7/2020 | De Groot |
| 2020/0229707 A1 | 7/2020 | Donnelly |
| 2020/0232959 A1 | 7/2020 | Armitage |
| 2020/0242551 A1 | 7/2020 | Lau et al. |
| 2020/0273047 A1 | 8/2020 | Bridge et al. |
| 2020/0281151 A1 | 9/2020 | Schmidt |
| 2020/0381119 A1 | 12/2020 | Gibbs et al. |
| 2021/0148891 A1 | 5/2021 | Beal |
| 2022/0020051 A1 | 1/2022 | Aruga et al. |
| 2022/0113296 A1 | 4/2022 | Beal |
| 2022/0228121 A1 | 7/2022 | Stout |

FOREIGN PATENT DOCUMENTS

| | | |
|---|---|---|
| AU | 2003238759 | 1/2004 |
| AU | 2004263067 | 2/2005 |
| AU | 2004305403 | 7/2005 |
| AU | 2011210083 | 8/2011 |
| AU | 2016266101 | 12/2016 |
| AU | 2017100469 | 5/2017 |
| AU | 2018220079 | 9/2018 |
| BR | 8701673 | 3/2009 |
| BR | 112012018909 | 1/2011 |
| CA | 2267812 | 10/2000 |
| CA | 2493331 | 1/2005 |
| CA | 2788153 | 8/2011 |
| CA | 2880138 | 2/2013 |
| CA | 2858905 | 10/2013 |
| CA | 2875637 | 1/2014 |
| CA | 2875578 | 12/2014 |
| CA | 2915843 | 12/2014 |
| CA | 2990620 | 12/2016 |
| CA | 2916286 | 6/2017 |
| CA | 3007296 | 6/2017 |
| CN | 1989895 | 7/2007 |
| CN | 201171316 | 12/2008 |
| CN | 101578516 | 11/2009 |
| CN | 101816290 | 9/2010 |
| CN | 101875975 | 11/2010 |
| CN | 101875976 | 11/2010 |
| CN | 102781225 | 1/2011 |
| CN | 102142116 | 8/2011 |
| CN | 102485892 | 6/2012 |
| CN | 102682322 | 9/2012 |
| CN | 203313865 | 12/2013 |
| CN | 203689049 | 2/2014 |
| CN | 203523519 | 4/2014 |
| CN | 204047531 | 8/2014 |
| CN | 204305813 | 5/2015 |
| CN | 204331349 | 5/2015 |
| CN | 105191817 | 12/2015 |
| CN | 106125648 | 11/2016 |
| CN | 106172068 | 12/2016 |
| CN | 106197675 | 12/2016 |
| CN | 106719037 | 2/2017 |
| CN | 205919898 | 2/2017 |
| CN | 106472347 | 3/2017 |
| CN | 106845598 | 6/2017 |
| CN | 206431665 | 8/2017 |
| CN | 107201409 | 9/2017 |
| CN | 207201674 | 9/2017 |
| CN | 107251851 | 10/2017 |
| CN | 107667898 | 2/2018 |
| CN | 108353810 | 2/2018 |
| CN | 207100094 | 3/2018 |
| CN | 207249710 | 4/2018 |
| CN | 108651301 | 5/2018 |
| CN | 108656996 | 5/2018 |
| CN | 108684549 | 5/2018 |
| CN | 108118096 | 6/2018 |
| CN | 108308055 | 7/2018 |

| | | |
|---|---|---|
| CN | 109006541 | 8/2018 |
| CN | 109008529 | 8/2018 |
| CN | 108617533 | 10/2018 |
| CN | 108717668 | 10/2018 |
| CN | 108766586 | 11/2018 |
| CN | 109006550 | 12/2018 |
| CN | 208273869 | 12/2018 |
| CN | 109355402 | 2/2019 |
| CN | 109937904 | 3/2019 |
| CN | 109937905 | 3/2019 |
| CN | 109823691 | 5/2019 |
| CN | 110073995 | 5/2019 |
| CN | 110059781 | 7/2019 |
| CN | 110106261 | 8/2019 |
| CN | 110106262 | 8/2019 |
| CN | 110506656 | 11/2019 |
| CN | 210076292 | 2/2020 |
| CN | 107205362 A | 1/2021 |
| DE | 633742 | 8/1936 |
| DE | 2850438 | 5/1980 |
| DE | 19629166 | 2/1997 |
| DE | 19826348 | 6/1998 |
| DE | 29906146 | 6/1999 |
| DE | 19911766 | 9/2000 |
| DE | 20018364 | 1/2001 |
| DE | 10001176 | 5/2001 |
| DE | 102004027978 | 12/2005 |
| DE | 202010008325 | 2/2012 |
| DE | 202013011075 | 1/2014 |
| DE | 202016101289 | 4/2016 |
| DK | 140001 | 11/1979 |
| EP | 55127 | 6/1982 |
| EP | 125915 | 11/1984 |
| EP | 0499428 | 8/1992 |
| EP | 513525 | 11/1992 |
| EP | 743043 | 11/1996 |
| EP | 938841 | 2/1998 |
| EP | 898449 | 3/1999 |
| EP | 1076485 | 2/2001 |
| EP | 1445723 | 8/2004 |
| EP | 1479338 | 11/2004 |
| EP | 1521208 | 4/2005 |
| EP | 1907816 | 4/2008 |
| EP | 1961294 | 8/2008 |
| EP | 2028931 | 3/2009 |
| EP | 2172878 | 4/2010 |
| EP | 2453733 | 5/2012 |
| EP | 2465344 | 6/2012 |
| EP | 2488237 | 8/2012 |
| EP | 2528431 | 12/2012 |
| EP | 2534945 | 12/2012 |
| EP | 2657889 | 10/2013 |
| EP | 2664234 | 11/2013 |
| EP | 2728995 | 5/2014 |
| EP | 2879615 | 6/2015 |
| EP | 2955998 | 12/2015 |
| EP | 3153098 | 4/2017 |
| EP | 3164855 | 5/2017 |
| EP | 3210531 | 8/2017 |
| EP | 3217566 | 9/2017 |
| EP | 3218865 | 9/2017 |
| EP | 3225106 | 10/2017 |
| EP | 3316680 | 5/2018 |
| EP | 3346422 | 7/2018 |
| EP | 3385886 | 10/2018 |
| EP | 3593634 | 1/2020 |
| EP | 3627856 | 3/2020 |
| EP | 3660855 | 6/2020 |
| EP | 4001951 A1 | 5/2022 |
| ES | 2046912 | 2/1994 |
| ES | 2206009 | 5/2004 |
| ES | 2215152 | 10/2004 |
| ES | 1072416 | 7/2010 |
| ES | 2391341 | 11/2012 |
| ES | 1194609 | 10/2017 |
| FI | 20165318 | 6/2017 |
| FR | 2106705 | 5/1972 |
| FR | 2297565 | 8/1976 |
| FR | 2342024 | 1/1983 |

(56) References Cited

FOREIGN PATENT DOCUMENTS

| | | |
|---|---|---|
| FR | 2601848 | 1/1988 |
| FR | 2779153 | 12/1999 |
| FR | 2834521 | 7/2003 |
| FR | 2964777 | 3/2012 |
| FR | 3046332 | 1/2016 |
| FR | 3024653 | 2/2016 |
| FR | 3085249 | 9/2018 |
| GB | 588870 | 6/1947 |
| GB | 641394 | 8/1950 |
| GB | 865164 | 4/1961 |
| GB | 1072971 | 6/1967 |
| GB | 1267830 | 3/1972 |
| GB | 1415650 | 11/1975 |
| GB | 2067121 | 7/1981 |
| GB | 2055670 | 7/1983 |
| GB | 2114045 | 8/1983 |
| GB | 2125343 | 3/1984 |
| GB | 2142812 | 1/1985 |
| GB | 2392138 | 2/2004 |
| GB | 2469326 | 10/2010 |
| GB | 2554636 | 9/2016 |
| GB | 2570340 | 7/2019 |
| GB | 2571404 | 8/2019 |
| IN | 201103443 | 12/2011 |
| IN | 200802272 | 6/2016 |
| JP | 57173562 | 11/1982 |
| JP | 7177832 | 7/1995 |
| JP | 2001178692 | 7/2001 |
| JP | 2004292151 | 10/2004 |
| JP | 2005102959 | 4/2005 |
| JP | 5659243 | 1/2011 |
| JP | 2011067178 | 4/2011 |
| JP | 2011087657 | 5/2011 |
| JP | 2013247941 | 6/2012 |
| JP | 2017112857 | 6/2017 |
| JP | 2017002170 | 4/2018 |
| KR | 2003061157 | 7/2003 |
| KR | 2005046330 | 5/2005 |
| KR | 780449 | 11/2007 |
| KR | 101747418 | 1/2011 |
| KR | 20130019970 | 2/2013 |
| KR | 20130057683 | 6/2013 |
| KR | 2013138899 | 12/2013 |
| KR | 2019061805 | 11/2017 |
| KR | 101827311 | 2/2018 |
| KR | 20180035537 | 4/2018 |
| KR | 2018109451 | 10/2018 |
| KR | 20190081598 | 7/2019 |
| KR | 2019091708 | 8/2019 |
| MX | 9600754 | 2/1997 |
| MX | 356331 | 1/2011 |
| NL | 2017104 | 1/2018 |
| NL | 2019186 | 1/2019 |
| NL | 2020275 | 7/2019 |
| NZ | 198486 | 5/1986 |
| NZ | 199494 | 7/1986 |
| NZ | 203924 | 10/1986 |
| NZ | 335702 | 3/2001 |
| NZ | 507129 | 8/2002 |
| NZ | 582984 | 1/2011 |
| RU | 2178711 | 1/2002 |
| RU | 2265324 | 12/2005 |
| RU | 694196 C1 | 7/2019 |
| RU | 2734321 C1 | 10/2020 |
| SE | 4567 | 3/1893 |
| SE | 5549 | 4/1894 |
| SE | 123213 | 11/1948 |
| SE | 188102 | 3/1964 |
| SU | 1766336 | 10/1992 |
| WO | 1984000468 | 2/1984 |
| WO | 1991011956 | 8/1991 |
| WO | 199302549 | 2/1993 |
| WO | 199822028 | 5/1998 |
| WO | 1998039475 | 9/1998 |
| WO | 1999017658 | 4/1999 |
| WO | 2000062263 | 4/1999 |
| WO | 9945761 | 9/1999 |
| WO | 2000013393 | 3/2000 |
| WO | 2000061802 | 10/2000 |
| WO | 2001033950 | 5/2001 |
| WO | 2001087054 | 11/2001 |
| WO | 2002031629 | 4/2002 |
| WO | 2002085106 | 10/2002 |
| WO | 2003001180 | 1/2003 |
| WO | 2004092920 | 3/2003 |
| WO | 2003087765 | 10/2003 |
| WO | 2003094605 | 11/2003 |
| WO | 2004015655 | 2/2004 |
| WO | 2005104775 | 4/2004 |
| WO | 2006078943 | 1/2005 |
| WO | 2005034617 A1 | 4/2005 |
| WO | 2005104930 | 4/2005 |
| WO | 2005073408 | 8/2005 |
| WO | 2005082132 A2 | 9/2005 |
| WO | 2006021855 | 3/2006 |
| WO | 20060036567 A1 | 4/2006 |
| WO | 2006134197 | 12/2006 |
| WO | 2006135265 | 12/2006 |
| WO | 2007034211 | 3/2007 |
| WO | 2007095684 | 8/2007 |
| WO | 2007122375 | 11/2007 |
| WO | 200801803 A2 | 2/2008 |
| WO | 2008033042 | 3/2008 |
| WO | 2008041839 A1 | 4/2008 |
| WO | 2008052298 | 5/2008 |
| WO | 2008075974 | 6/2008 |
| WO | 2010091686 | 12/2008 |
| WO | 2009034497 | 3/2009 |
| WO | 2009062249 | 5/2009 |
| WO | 2009076325 | 6/2009 |
| WO | 2009089215 | 7/2009 |
| WO | 2009117764 | 10/2009 |
| WO | 2009153779 | 12/2009 |
| WO | 2010008620 | 1/2010 |
| WO | 2010048753 | 5/2010 |
| WO | 2010053811 | 5/2010 |
| WO | 2010068713 | 6/2010 |
| WO | 2010140900 | 12/2010 |
| WO | 2012075480 | 12/2010 |
| WO | 2011039112 | 4/2011 |
| WO | 2011076886 | 6/2011 |
| WO | 2011154949 | 12/2011 |
| WO | 2012071670 | 6/2012 |
| WO | 2013008115 | 1/2013 |
| WO | 2013038326 | 3/2013 |
| WO | 2013082227 | 6/2013 |
| WO | 2015001537 | 7/2013 |
| WO | 2013118121 | 8/2013 |
| WO | 2013122468 A1 | 8/2013 |
| WO | 2015024050 | 8/2013 |
| WO | 2013179020 | 12/2013 |
| WO | 2013190423 | 12/2013 |
| WO | 2014020463 | 2/2014 |
| WO | 2014095759 | 6/2014 |
| WO | 2014107766 | 7/2014 |
| WO | 2014118788 | 8/2014 |
| WO | 2014125250 | 8/2014 |
| WO | 2016027271 | 8/2014 |
| WO | 2014140148 | 9/2014 |
| WO | 2014141084 | 9/2014 |
| WO | 2014194383 | 12/2014 |
| WO | 2014197631 | 12/2014 |
| WO | 2014199363 | 12/2014 |
| WO | 2015009167 | 1/2015 |
| WO | 2015030832 | 3/2015 |
| WO | 2015055709 | 4/2015 |
| WO | 2015086338 | 6/2015 |
| WO | 2016207844 | 6/2015 |
| WO | 2015107354 | 7/2015 |
| WO | 2017001717 | 7/2015 |
| WO | 2017031532 | 8/2015 |
| WO | 2015140486 | 9/2015 |
| WO | 2015158787 | 10/2015 |
| WO | 2015175686 | 11/2015 |

(56) References Cited

FOREIGN PATENT DOCUMENTS

| WO | 2015176027 | | 11/2015 |
|----|------------|-----|---------|
| WO | 2015197385 | | 12/2015 |
| WO | 2016005911 | A1 | 1/2016 |
| WO | 2016037190 | | 3/2016 |
| WO | 2017149049 | | 3/2016 |
| WO | 2016053104 | | 4/2016 |
| WO | 2016108187 | | 7/2016 |
| WO | 2016166748 | | 10/2016 |
| WO | 2017001538 | | 1/2017 |
| WO | 2017027551 | | 2/2017 |
| WO | 2017037479 | | 3/2017 |
| WO | 2017066813 | | 4/2017 |
| WO | 2017089289 | | 6/2017 |
| WO | 2017096256 | | 6/2017 |
| WO | 2017/122097 | A1 | 7/2017 |
| WO | 2017121834 | | 7/2017 |
| WO | 2018006965 | | 1/2018 |
| WO | 2018011736 | | 1/2018 |
| WO | 2018019742 | | 2/2018 |
| WO | 2020022543 | | 7/2018 |
| WO | 2018172976 | | 9/2018 |
| WO | 2020060248 | | 9/2018 |
| WO | 2018203203 | | 11/2018 |
| WO | 2019009717 | | 1/2019 |
| WO | 2019025138 | | 2/2019 |
| WO | 2019046216 | | 3/2019 |
| WO | 2019048521 | A1 | 3/2019 |
| WO | 2019058752 | | 3/2019 |
| WO | 2019068178 | A1 | 4/2019 |
| WO | 2019071222 | | 4/2019 |
| WO | 2019132803 | | 7/2019 |
| WO | 2019207561 | | 10/2019 |
| WO | 2019226100 | A1 | 11/2019 |
| WO | 2019235942 | | 12/2019 |
| WO | 2019245978 | | 12/2019 |
| WO | 2020003310 | | 1/2020 |
| WO | 2020096528 | | 5/2020 |
| WO | 2020140013 | | 7/2020 |
| WO | 2021097388 | A1 | 5/2021 |

OTHER PUBLICATIONS

Christian Pahl, Eberhard Hartung, Anne Grothmann, Katrin Mahlkow-Nerge, Angelika Haeussermann, Rumination activity of dairy cows in the 24 hours before and after calving, Journal of Dairy Science, vol. 97, Issue 11, 2014, pp. 6935-6941.

Steensels, Machteld; Maltz, Ephraim; Bahr, Claudia; Berckmans, Daniel; Antler, Aharon; et al., Towards practical application of sensors for monitoring animal health: The effect of post-calving health problems on rumination duration, activity and milk yield, The Journal of Dairy Research; Cambridge vol. 84, Iss. 2, (May 2017): 132-138.

Clark, C., Lyons, N., Millapan, L., Talukder, S., Cronin, G., Kerrisk, K., Garcia, S. (2015), Rumination and activity levels as predictors of calving for dairy cows, 9(4), 691-695.

Koyama, T. Koyama, M. Sugimoto, N. Kusakari, R. Miura, K. Yoshioka, M. Hirako, Prediction of calving time in Holstein dairy cows by monitoring the ventral tail base surface temperature, The Veterinary Journal, vol. 240, 2018, pp. 1-5, ISSN 1090-0233.

L. Calamari, N. Soriani, G. Panella, F. Petrera, A. Minuti, E. Trevisi, Rumination time around calving: An early signal to detect cows at greater risk of disease, Journal of Dairy Science, vol. 97, Issue 6, 2014, pp. 3635-3647, ISSN 0022-0302.

S. Benaissa, F.A.M. Tuyttens, D. Plets, J. Trogh, L. Martens, L. Vandaele, W. Joseph, B. Sonck, Calving and estrus detection in dairy cattle using a combination of indoor localization and accelerometer sensors, Computers and Electronics in Agriculture, vol. 168, 2020, 105153, ISSN 0168-1699.

N. Soriani, E. Trevisi, L. Calamari, Relationships between rumination time, metabolic conditions, and health status in dairy cows during the transition period, Journal of Animal Science, vol. 90, Issue 12, Dec. 2012, pp. 4544-4554.

The role of sensors, big data and machine learning in modern animal farming; Suresh Neethirajan; Received Jun. 2, 2020; Received in revised form Jun. 30, 2020; Accepted Jul. 3, 2020 Sensing and Bio-Sensing Research 29 (2020) 1003672214-1804/ © 2020 The Author. Published by Elsevier B.V.

A Review on Determination of Computer Aid Diagnosis and/or Risk Factors Using Data Mining Methods in Veterinary Field Pnar Cihan, Erhan Gökçe, Oya Kalipsiz; Tekirdağ Namik Kemal University, Çorlu Faculty of Engineering, Department of Computer Engineering, Tekirdağ, Turkey. 2019.

Big Data Analytics and Precision Animal Agriculture Symposium: Data to decisions B. J. White, D. E. Amrine, and R. L. Larson Beef Cattle Institute, Kansas State University, Manhattan, KS; © The Author(s) 2018. Published by Oxford University Press on behalf of American Society of Animal Science.

Gasteiner, J.; Boswerger, B.; Guggenberger, T., Practical use of a novel ruminal sensor on dairy farms, Praktische Tierarzt 2012 vol. 93 No. 8 pp. 730 . . . 739 ref.45.

Drying up Cows and The Effect of Different Methods Upon Milk Production; Ralph Wayne, C. H. Eckles, and W. E. Peterson; Division of Dairy Husbandry, University of Minnesota, St. Paul; Research-Article|vol. 16, Issue 1, p. 69-78, Jan. 1, 1933.

Eagan, B. H., B. Eagan, and A. Protopopova. "Behaviour Real-Time spatial tracking identification (BeRSTID) used for cat behaviour monitoring in an animal shelter." Scientific reports 12.1 (2022): 17585.

Garrido-Jurado, Sergio, et al. "Automatic generation and detection of highly reliable fiducial markers under occlusion." Pattern Recognition 47.6 (2014): 2280-2292.

Steve Nadis. "Invisible machine-readable labels that identify and track objects". Retrieved online on Sep. 3, 2023. URL: https://www.wevolver.com/article/invisible-machine-readable-labelsthat-identify-and-track-objects.

Dougherty, C.T. et al., Face flies (*Musca autumnalis* De Geer) and the behavior of grazing beef cattle, Applied Animal Behaviour Science, 35, 313-326, 1993.

Eicher, S.D. et al., Tail-Docking Alters Fly Numbers, Fly• avoidance behaviors, and Cleanliness, but not Physiological Measures, J. Dairy Sci., 84, 1822-1828, 2001.

GpTrac Great Plains Telehealth Resource and Assistance Center, Remote Patient Monitoring, Toolkit Series, Apr. 2021. (Year: 2021).

* cited by examiner

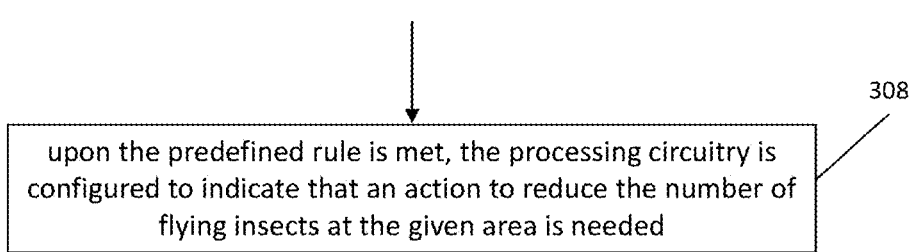
308
upon the predefined rule is met, the processing circuitry is configured to indicate that an action to reduce the number of flying insects at the given area is needed
FIG. 5
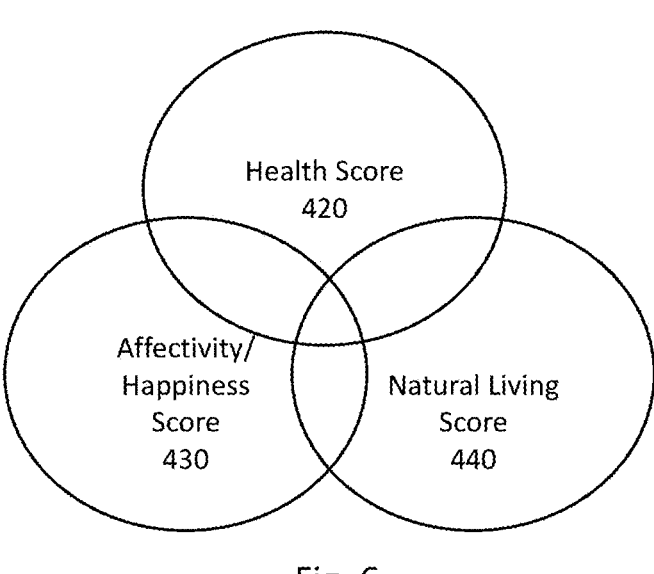
Health Score
420
Affectivity/
Happiness
Score
430
Natural Living
Score
440
Fig. 6
Network Interface
520
Welfare KPIs
Determination
Module
540
Data Repository
510
Processing Circuitry 530
Welfare Determination System 500
Fig. 7

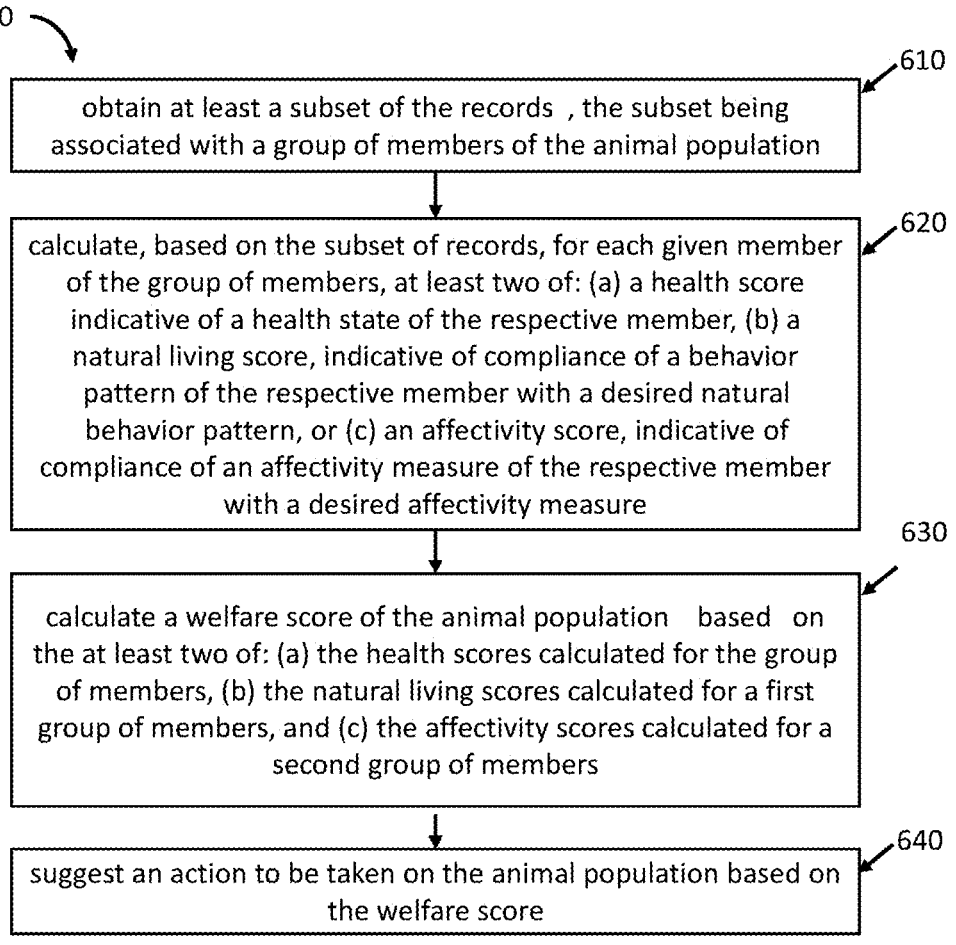

600

610
obtain at least a subset of the records , the subset being associated with a group of members of the animal population 620
calculate, based on the subset of records, for each given member of the group of members, at least two of: (a) a health score indicative of a health state of the respective member, (b) a natural living score, indicative of compliance of a behavior pattern of the respective member with a desired natural behavior pattern, or (c) an affectivity score, indicative of compliance of an affectivity measure of the respective member with a desired affectivity measure 630
calculate a welfare score of the animal population   based   on the at least two of: (a) the health scores calculated for the group of members, (b) the natural living scores calculated for a first group of members, and (c) the affectivity scores calculated for a second group of members 640
suggest an action to be taken on the animal population based on the welfare score

Fig. 8

SYSTEM AND METHOD FOR EVALUATING THE LEVEL OF HARASSMENT OF INSECTS ON A PLURALITY OF ANIMALS

TECHNICAL FIELD

The present invention relates to the field of evaluating the level of harassment of flying insects.

BACKGROUND

Insects are pan crustacean hexapod invertebrates of the class Insecta having a chitinous exoskeleton, a three-part body (head, thorax, and abdomen), three pairs of jointed legs, compound eyes, and one pair of antennae. Insects are the most diverse group of animals including more than a million described species representing more than half of all known living organisms.

During their developmental process, insects go through several stages ranging from the initial egg or embryo stage to the final adult stage, where most insects have wings. This makes flying the preferable form of movement for most adult insects, though walking, or sometimes swimming are also forms of movement in which they move about.

While most flying insects may be a nuisance to other animals, some flying insects pose an additional risk to the health and well-being of other animals. For example, flies of all kinds cause actual irritation to farm animals (e.g., goats, sheep, cows, and the like), prompting them to consume less food (resulting in a slower growth rate) and produce less milk. In doing so, flies are estimated to be responsible for the loss of billions of dollars each year worldwide. In addition, due to their known role as disease spreaders, flying insects, which are known pathogens capable of carrying diseases such as keratoconjunctivitis (pinkeye), summer mastitis and the like, can have a direct effect on the health of other animals.

As current solutions are primarily focused on pest control and reducing the number of potentially harmful flying insects, regardless of the level of harassment these insects pose, these solutions fail in providing a tool for evaluating the level of harassment inflicted to animals by potentially harmful flying insects. Furthermore, none of the current solutions is based on direct measurements acquired from animals of an animal population, which enable determining the level of harassment of flying insects on the animal population in a given area. Likewise, none of the current solutions involves considering the level of harassment pose by flying insects when trying to assess a welfare of the animal population (harassment caused by flying insects is known to increase the stress levels of the animal population and, by that, impact the population's health), and/or the distribution of a given disease within the animal population.

Thus, there is a need in the art for a system and method for evaluating the level of harassment of flying insects on a plurality of animals in a given area.

GENERAL DESCRIPTION

In accordance with a first aspect of the presently disclosed subject matter, there is provided a system for evaluating the level of harassment of flying insects on a plurality of animals located at a given area, the system comprising a processing circuitry configured to: obtain one or more ear movement patterns associated with at least one ear of at least one animal of the plurality of animals, each ear movement pattern is associated with respective ear movement characteristics; for at least part of the one or more ear movement patterns, determine whether their respective ear movement characteristics meet a predefined rule; and, determine whether a number of ear movement patterns whose ear movement characteristics met the predefined rule meets an action requirement rule.

In one embodiment of the presently disclosed subject matter and/or embodiments thereof, each of the one or more ear movement patterns is associated with its own characteristics.

In one embodiment of the presently disclosed subject matter and/or embodiments thereof, the one or more ear movement patterns are associated with characteristics common to all ear movement patterns.

In one embodiment of the presently disclosed subject matter and/or embodiments thereof, the action requirement rule is one of: (a) the number of ear movement patterns whose characteristics met the predefined rule is above a first harassment threshold, (b) a percentage of the number of ear movement patterns whose characteristics met the predefined rule from a number of the plurality of animals is above a second harassment threshold.

In one embodiment of the presently disclosed subject matter and/or embodiments thereof, upon the action requirement rule is met, the processing circuitry is configured to indicate that an action to reduce the number of flying insects at the given area is needed.

In one embodiment of the presently disclosed subject matter and/or embodiments thereof, the action includes at least one of: installing flying insects' papers, installing flying insects' traps, installing pesticide-releasing flying insects' strips, using repellent flying insects' sprays, using flying insects' predators, or any combination thereof.

In one embodiment of the presently disclosed subject matter and/or embodiments thereof, the action is directed to attend to one or more health conditions.

In one embodiment of the presently disclosed subject matter and/or embodiments thereof, the obtaining of the ear movement pattern of the at least one ear is achieved via at least one respective accelerometer coupled to the at least one ear.

In some cases, the at least one respective accelerometer is part of at least one respective ear tag attached to the at least one ear of at least one animal.

In one embodiment of the presently disclosed subject matter and/or embodiments thereof, the flying insects are any one of house flies, stable flies, blow flies, flesh flies, cluster flies, or any combination thereof.

In one embodiment of the presently disclosed subject matter and/or embodiments thereof, the one or more animals are any one of livestock animals, domesticated animals, wild animals, and a combination thereof.

In one embodiment of the presently disclosed subject matter and/or embodiments thereof, the one or more animals are dairy cows.

In one embodiment of the presently disclosed subject matter and/or embodiments thereof, the given area is a controlled environment.

In accordance with a second aspect of the presently disclosed subject matter, there is provided a method for evaluating the level of harassment of flying insects on a plurality of animals located at a given area, the method comprising: obtaining one or more ear movement patterns associated with at least one ear of at least one animal of the plurality of animals, each ear movement pattern is associated with respective ear movement characteristics; for at least part of the one or more ear movement patterns, determining whether their respective ear movement characteristics meet a predefined rule; and, determining whether a number of ear movement patterns whose ear movement characteristics met the predefined rule meets an action requirement rule.

In one embodiment of the presently disclosed subject matter and/or embodiments thereof, the one or more ear movement patterns are associated with characteristics common to all ear movement patterns.

In one embodiment of the presently disclosed subject matter and/or embodiments thereof, each of the one or more ear movement patterns is associated with its own characteristics.

In one embodiment of the presently disclosed subject matter and/or embodiments thereof, the action requirement rule is one of: (a) the number of ear movement patterns whose characteristics met the predefined rule is above a first harassment threshold, (b) a percentage of the number of ear movement patterns whose characteristics met the predefined rule from a number of the plurality of animals is above a second harassment threshold.

In one embodiment of the presently disclosed subject matter and/or embodiments thereof, upon the action requirement rule is met, the method involves indicating that an action to reduce the number of flying insects at the given area is needed.

In one embodiment of the presently disclosed subject matter and/or embodiments thereof, the action includes at least one of: installing flying insects' papers, installing flying insects' traps, installing pesticide-releasing flying insects' strips, using repellent flying insects' sprays, using flying insects' predators, or any combination thereof.

In one embodiment of the presently disclosed subject matter and/or embodiments thereof, the obtaining of the ear movement pattern of the at least one ear is achieved via at least one respective accelerometer coupled to the at least one ear.

In one embodiment of the presently disclosed subject matter and/or embodiments thereof, the at least one respective accelerometer is part of at least one respective ear tag attached to the at least one ear of at least one animal.

In one embodiment of the presently disclosed subject matter and/or embodiments thereof, the flying insects are any one of house flies, stable flies, blow flies, flesh flies, cluster flies, or any combination thereof.

In one embodiment of the presently disclosed subject matter and/or embodiments thereof, the one or more animals are any one of livestock animals, domesticated animals, wild animals, and a combination thereof.

In one embodiment of the presently disclosed subject matter and/or embodiments thereof, the one or more animals are dairy cows.

In one embodiment of the presently disclosed subject matter and/or embodiments thereof, the given area is a controlled environment.

In accordance with a third aspect of the presently disclosed subject matter, there is provided a non-transitory computer readable storage medium having computer readable program code embodied therewith, the computer readable program code, executable by at least one processor to perform a method for evaluating the level of harassment of flying insects on a plurality of animals located at a given area, the harassment evaluation comprising one or more components, the method comprising: obtaining one or more ear movement patterns associated with at least one ear of at least one animal of the plurality of animals, each ear movement pattern is associated with respective ear movement characteristics; for at least part of the one or more ear movement patterns, determining whether their respective ear movement characteristics meet a predefined rule; and, determining whether a number of ear movement patterns whose ear movement characteristics met the predefined rule meets an action requirement rule.

In accordance with a fourth aspect of the presently disclosed subject matter, there is provided a system for determining a welfare of an animal population, the system comprising: one or more monitoring devices configured to monitor parameters of members of the animal population; a data repository comprising one or more records, each of the records (i) being associated with a respective member of the members, and (ii) including one or more parameters of the respective member as monitored by at least one of the monitoring devices over time; and a processing circuitry configured to: obtain at least a subset of the records, the subset being associated with a first group of members of the animal population; calculate: (A) based on the subset of records, for each given member of the first group of members, at least two of: (a) a health score indicative of a health state of the respective member, (b) a natural living score, indicative of compliance of a behavior pattern of the respective member with a desired natural behavior pattern, or (c) an affectivity/happiness score, indicative of compliance of an affectivity/happiness measure of the respective member with a desired affectivity/happiness measure; and (B) a welfare score of the animal population based on the at least two of: (a) the health scores calculated for the first group of members, (b) the natural living scores calculated for a second group of members, or (c) the affectivity/happiness scores calculated for a third group of members.

In one embodiment of the presently disclosed subject matter and/or embodiments thereof, the parameters include one or more of the following behavioral parameters: (a) percentage of movement time within a first time period of the given member, (b) percentage of feeding time within a second time period of the given member or (c) percentage of social behavior time within a third time period of the given member; and wherein the natural living score for the given member is determined based on the behavioral parameters.

In one embodiment of the presently disclosed subject matter and/or embodiments thereof, the natural living score for the given member is determined based on consistency of values of at least some of the parameters over time.

In one embodiment of the presently disclosed subject matter and/or embodiments thereof, the consistency of the values is measured against reference parameters.

In one embodiment of the presently disclosed subject matter and/or embodiments thereof, the reference parameters are measured from reference animals.

In one embodiment of the presently disclosed subject matter and/or embodiments thereof, the parameters include one or more of the following affectivity/happiness parameters: (a) respiration level of the given member, (b) percentage of rumination time within a fourth time period of the given member, or (c) percentage of feeding time within a fifth time period of the given member; and wherein the affectivity/happiness score for the given member is determined based on the affectivity/happiness parameters.

In one embodiment of the presently disclosed subject matter and/or embodiments thereof, the affectivity/happiness score for the given member is determined based on consistency of values of at least some of the parameters over time.

In one embodiment of the presently disclosed subject matter and/or embodiments thereof, the consistency of the values is measured against reference parameters.

In one embodiment of the presently disclosed subject matter and/or embodiments thereof, the reference parameters are measured from reference animals.

In one embodiment of the presently disclosed subject matter and/or embodiments thereof, the welfare score is calculated based on a variation between the affectivity/happiness scores of the first group of the members.

In one embodiment of the presently disclosed subject matter and/or embodiments thereof, at least two of the first group, the second group and the third group are identical groups.

In one embodiment of the presently disclosed subject matter and/or embodiments thereof, the second group and the third group comprise healthy members of the first group of members, having health scores above a threshold.

In one embodiment of the presently disclosed subject matter and/or embodiments thereof, the records also include one or more environmental parameters, indicative of the state of the environment of the respective member and wherein the determination of (a) the natural living score of the respective member or (b) of the affectivity/happiness score of the respective member, is also based on the environmental parameters.

In one embodiment of the presently disclosed subject matter and/or embodiments thereof, the monitoring device includes one or more of: an accelerometer, a temperature sensor, a location sensor, a pedometer, or a heart rate sensor.

In one embodiment of the presently disclosed subject matter and/or embodiments thereof, at least some of the records further include descriptive data associated with the respective member, wherein the descriptive data is not obtained from the monitoring device.

In one embodiment of the presently disclosed subject matter and/or embodiments thereof, the descriptive data includes one or more of: age of the respective member, sex of the respective member, treatment history of the respective member, or genetic information associated with the respective member.

In one embodiment of the presently disclosed subject matter and/or embodiments thereof, the processing circuitry is further configured to suggest an action to be taken on the animal population based on the welfare score.

In one embodiment of the presently disclosed subject matter and/or embodiments thereof, the action is one or more of: a treatment to be administered to the animal population, a change in temperature of an environment of the animal population, a change in feed of the animal population, or a change in a schedule of the animal population.

In one embodiment of the presently disclosed subject matter and/or embodiments thereof, the at least subset of the records are all the records of the animal population.

In one embodiment of the presently disclosed subject matter and/or embodiments thereof, the animal population is located in one or more geographical sites.

In one embodiment of the presently disclosed subject matter and/or embodiments thereof, at least some of the monitoring devices are attached monitoring devices, attached to respective members.

In one embodiment of the presently disclosed subject matter and/or embodiments thereof, the attached monitoring devices are monitoring tags or monitoring collars.

In one embodiment of the presently disclosed subject matter and/or embodiments thereof, the animal population is a population of ruminating animals or companion animals.

In one embodiment of the presently disclosed subject matter and/or embodiments thereof, the suggestion is given upon the welfare score being below a welfare threshold.

In one embodiment of the presently disclosed subject matter and/or embodiments thereof, the welfare threshold is determined based on statistical analysis of historical welfare scores.

In one embodiment of the presently disclosed subject matter and/or embodiments thereof, the welfare threshold is geographical location specific.

In accordance with a fifth aspect of the presently disclosed subject matter, there is provided a method for determining a welfare of an animal population, the method comprising: obtaining, by a processing circuitry, at least a subset of a group of one or more records, each of the records (i) being associated with a respective member of the members, and (ii) including one or more parameters of the respective member as monitored over time by at least one of a group of one or more monitoring devices configured to monitor parameters of members of the animal population, wherein the subset is associated with a first group of members of the animal population; calculating, by the processing circuitry: (A) based on the subset of records, for each given member of the first group of members, at least two of: (a) a health score indicative of a health state of the respective member, (b) a natural living score, indicative of compliance of a behavior pattern of the respective member with a desired natural behavior pattern, or (c) an affectivity/happiness score, indicative of compliance of an affectivity/happiness measure of the respective member with a desired affectivity/happiness measure; and (B) a welfare score of the animal population based on the at least two of: (a) the health scores calculated for the first group of members, (b) the natural living scores calculated for a second group of members, or (c) the affectivity/happiness scores calculated for a third group of members.

In one embodiment of the presently disclosed subject matter and/or embodiments thereof, the parameters include one or more of the following behavioral parameters: (a) percentage of movement time within a first time period of the given member, (b) percentage of feeding time within a second time period of the given member or (c) percentage of social behavior time within a third time period of the given member; and wherein the natural living score for the given member is determined based on the behavioral parameters.

In one embodiment of the presently disclosed subject matter and/or embodiments thereof, the natural living score for the given member is determined based on consistency of values of at least some of the parameters over time.

In one embodiment of the presently disclosed subject matter and/or embodiments thereof, the consistency of the values is measured against reference parameters.

In one embodiment of the presently disclosed subject matter and/or embodiments thereof, the reference parameters are measured from reference animals.

In one embodiment of the presently disclosed subject matter and/or embodiments thereof, the parameters include one or more of the following affectivity/happiness parameters: (a) respiration level of the given member, (b) percentage of rumination time within a fourth time period of the given member, or (c) percentage of feeding time within a fifth time period of the given member; and wherein the affectivity/happiness score for the given member is determined based on the affectivity/happiness parameters.

In one embodiment of the presently disclosed subject matter and/or embodiments thereof, the affectivity/happiness score for the given member is determined based on consistency of values of at least some of the parameters over time.

In one embodiment of the presently disclosed subject matter and/or embodiments thereof, the consistency of the values is measured against reference parameters.

In one embodiment of the presently disclosed subject matter and/or embodiments thereof, the reference parameters are measured from reference animals.

In one embodiment of the presently disclosed subject matter and/or embodiments thereof, the welfare score is calculated based on a variation between the affectivity/happiness scores of the first group of the members.

In one embodiment of the presently disclosed subject matter and/or embodiments thereof, at least two of the first group, the second group and the third group are identical groups.

In one embodiment of the presently disclosed subject matter and/or embodiments thereof, the second group and the third group comprise healthy members of the first group of members, having health scores above a threshold.

In one embodiment of the presently disclosed subject matter and/or embodiments thereof, the records also include one or more environmental parameters, indicative of the state of the environment of the respective member and wherein the determination of (a) the natural living score of the respective member or (b) of the affectivity/happiness score of the respective member, is also based on the environmental parameters.

In one embodiment of the presently disclosed subject matter and/or embodiments thereof, the monitoring device includes one or more of: an accelerometer, a temperature sensor, a location sensor, a pedometer, or a heart rate sensor.

In one embodiment of the presently disclosed subject matter and/or embodiments thereof, at least some of the records further include descriptive data associated with the respective member, wherein the descriptive data is not obtained from the monitoring device.

In one embodiment of the presently disclosed subject matter and/or embodiments thereof, the descriptive data includes one or more of: age of the respective member, sex of the respective member, treatment history of the respective member, or genetic information associated with the respective member.

In one embodiment of the presently disclosed subject matter and/or embodiments thereof, the method further comprises suggesting an action to be taken on the animal population based on the welfare score.

In one embodiment of the presently disclosed subject matter and/or embodiments thereof, the action is one or more of: a treatment to be administered to the animal population, a change in temperature of an environment of the animal population, a change in feed of the animal population, or a change in a schedule of the animal population.

In one embodiment of the presently disclosed subject matter and/or embodiments thereof, the at least subset of the records are all the records of the animal population.

In one embodiment of the presently disclosed subject matter and/or embodiments thereof, the animal population is located in one or more geographical sites.

In one embodiment of the presently disclosed subject matter and/or embodiments thereof, at least some of the monitoring devices are attached monitoring devices, attached to respective members.

In one embodiment of the presently disclosed subject matter and/or embodiments thereof, the attached monitoring devices are monitoring tags or monitoring collars.

In one embodiment of the presently disclosed subject matter and/or embodiments thereof, the animal population is a population of ruminating animals or companion animals.

In one embodiment of the presently disclosed subject matter and/or embodiments thereof, the suggestion is given upon the welfare score being below a welfare threshold.

In one embodiment of the presently disclosed subject matter and/or embodiments thereof, the welfare threshold is determined based on statistical analysis of historical welfare scores.

In one embodiment of the presently disclosed subject matter and/or embodiments thereof, the welfare threshold is geographical location specific.

In accordance with a sixth aspect of the presently disclosed subject matter, there is provided a non-transitory computer readable storage medium having computer readable program code embodied therewith, the computer readable program code, executable by at least one processing circuitry of a computer to perform a method for determining a welfare of an animal population, the method comprising: obtaining, by a processing circuitry, at least a subset of a group of one or more records, each of the records (i) being associated with a respective member of the members, and (ii) including one or more parameters of the respective member as monitored over time by at least one of a group of one or more monitoring devices configured to monitor parameters of members of the animal population, wherein the subset is associated with a first group of members of the animal population; calculating, by the processing circuitry: (A) based on the subset of records, for each given member of the first group of members, at least two of: (a) a health score indicative of a health state of the respective member, (b) a natural living score, indicative of compliance of a behavior pattern of the respective member with a desired natural behavior pattern, or (c) an affectivity/happiness score, indicative of compliance of an affectivity/happiness measure of the respective member with a desired affectivity/happiness measure; and (B) a welfare score of the animal population based on the at least two of: (a) the health scores calculated for the first group of members, (b) the natural living scores calculated for a second group of members, or (c) the affectivity/happiness scores calculated for a third group of members.

BRIEF DESCRIPTION OF THE DRAWINGS

In order to understand the presently disclosed subject matter and to see how it may be carried out in practice, the subject matter will now be described, by way of non-limiting examples only, with reference to the accompanying drawings, in which:

FIG. 5 is a flowchart illustrating another example of a sequence of operations carried out by a system for evaluating the level of harassment of flying insects on a plurality of animals in a given area, in accordance with the presently disclosed subject matter;

FIG. 6 is a schematic illustration of components of a welfare score for an animal population, in accordance with the presently disclosed subject matter;

FIG. 7 is a block diagram schematically illustrating one example of a welfare determination system for determining the welfare of an animal population, in accordance with the presently disclosed subject matter;

FIG. 8 is a flowchart illustrating one example of a sequence of operations carried out for determining the welfare of an animal population, in accordance with the presently disclosed subject matter;

DETAILED DESCRIPTION

Figure 1:
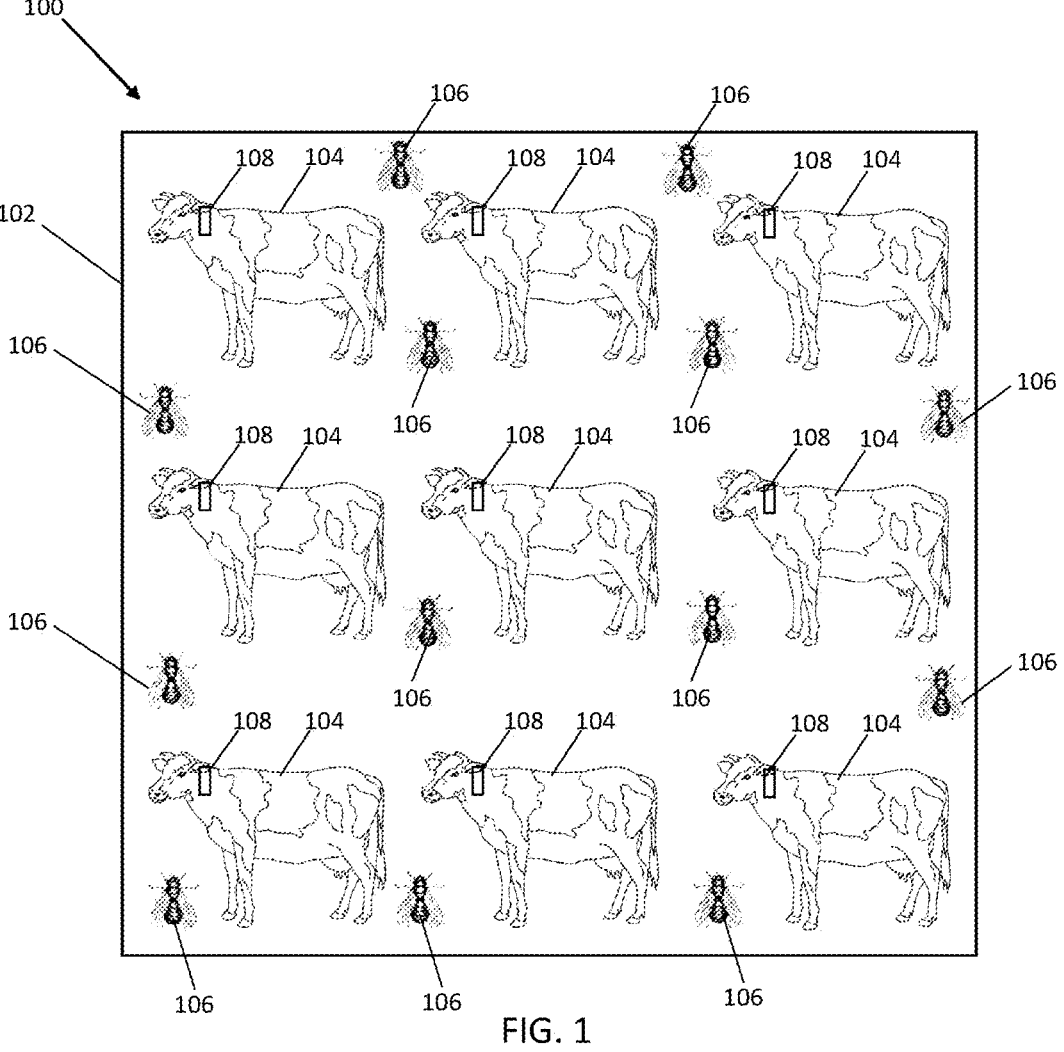
FIG. 1 is a schematic illustration of an environment in which the system for evaluating the level of harassment of flying insects on a plurality of animals in a given area operates, in accordance with the presently disclosed subject matter.

In the following detailed description, numerous specific details are set forth in order to provide a thorough understanding of the presently disclosed subject matter. However, it will be understood by those skilled in the art that the presently disclosed subject matter may be practiced without these specific details. In other instances, well-known methods, procedures, and components have not been described in detail so as not to obscure the presently disclosed subject matter.

In the drawings and descriptions set forth, identical reference numerals indicate those components that are common to different embodiments or configurations.

Unless specifically stated otherwise, as apparent from the following discussions, it is appreciated that throughout the specification discussions utilizing terms such as "obtaining", "determining", "indicating", "inserting", "analyzing", "providing", "calculating", "suggesting" or the like, include action and/or processes of a computer that manipulate and/or transform data into other data, said data represented as physical quantities, e.g., such as electronic quantities, and/or said data representing the physical objects. The terms "computer", "processor", "processing resource", "processing circuitry", and "controller" should be expansively construed to cover any kind of electronic device with data processing capabilities, including, by way of non-limiting example, a personal desktop/laptop computer, a server, a computing system, a communication device, a smartphone, a tablet computer, a smart television, a processor (e.g. digital signal processor (DSP), a microcontroller, a field programmable gate array (FPGA), an application specific integrated circuit (ASIC), etc.), a group of multiple physical machines sharing performance of various tasks, virtual servers co-residing on a single physical machine, any other electronic computing device, and/or any combination thereof.

The operations in accordance with the teachings herein may be performed by a computer specially constructed for the desired purposes or by a general-purpose computer specially configured for the desired purpose by a computer program stored in a non-transitory computer readable storage medium. The term "non-transitory" is used herein to exclude transitory, propagating signals, but to otherwise include any volatile or non-volatile computer memory technology suitable to the application.

As used herein, the phrase "for example," "such as", "for instance" and variants thereof describe non-limiting embodiments of the presently disclosed subject matter. Reference in the specification to "one case", "some cases", "other cases" or variants thereof means that a particular feature, structure or characteristic described in connection with the embodiment(s) is included in at least one embodiment of the presently disclosed subject matter. Thus, the appearance of the phrase "one case", "some cases", "other cases" or variants thereof does not necessarily refer to the same embodiment(s).

It is appreciated that, unless specifically stated otherwise, certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable sub-combination.

Figure 2:
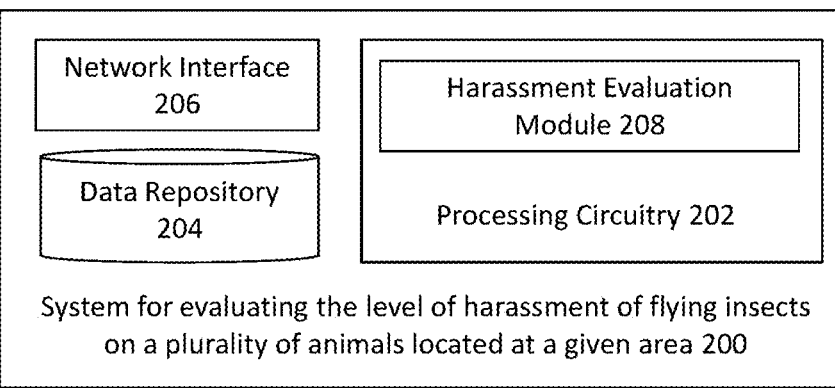
FIG. 2 is a block diagram schematically illustrating one example of a system evaluating the level of harassment of flying insects on a plurality of animals in a given area, in accordance with the presently disclosed subject matter.
Figure 3:
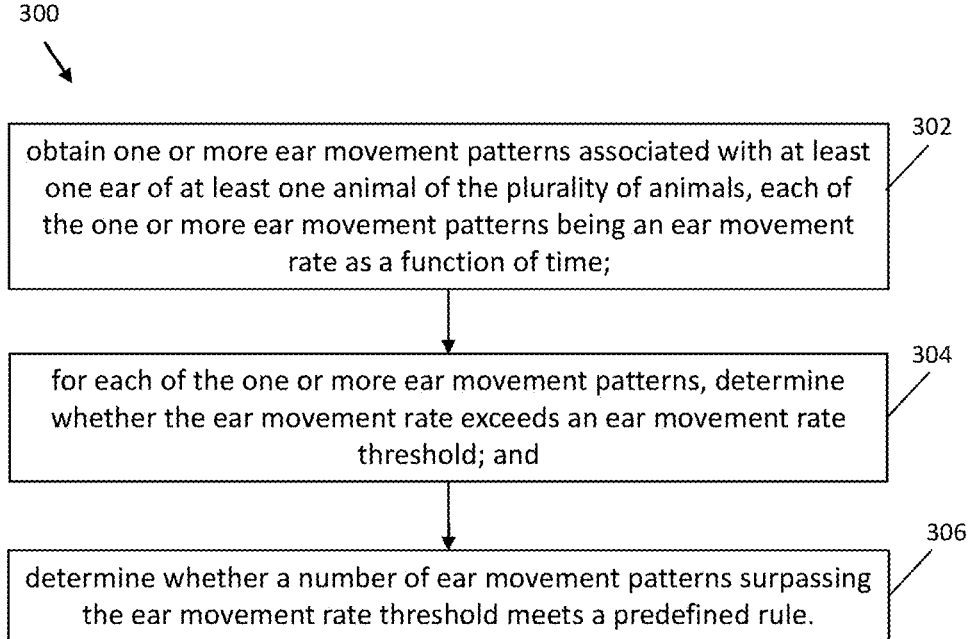
FIG. 3 is a flowchart illustrating an example of a sequence of operations carried out by a system for evaluating the level of harassment of flying insects on a plurality of animals in a given area, in accordance with the presently disclosed subject matter.

In embodiments of the presently disclosed subject matter, fewer, more and/or different stages than those shown in FIGS. 3, 5 and 8 may be executed. In embodiments of the presently disclosed subject matter one or more stages illustrated in FIGS. 3, 5 and 8 may be executed in a different order and/or one or more groups of stages may be executed simultaneously. FIGS. 2 and 7 illustrate general schematics of the systems architecture in accordance with an embodiment of the presently disclosed subject matter. Each module in FIGS. 2 and 7 can be made up of any combination of software, hardware and/or firmware that performs the functions as defined and explained herein. The modules in FIGS. 2 and 7 may be centralized in one location or dispersed over more than one location. In other embodiments of the presently disclosed subject matter, the system may comprise fewer, more, and/or different modules than those shown in FIGS. 2 and 7.

Any reference in the specification to a method should be applied mutatis mutandis to a system capable of executing the method and should be applied mutatis mutandis to a non-transitory computer readable medium that stores instructions that once executed by a computer result in the execution of the method.

Any reference in the specification to a system should be applied mutatis mutandis to a method that may be executed by the system and should be applied mutatis mutandis to a non-transitory computer readable medium that stores instructions that may be executed by the system.

Any reference in the specification to a non-transitory computer readable medium should be applied mutatis mutandis to a system capable of executing the instructions stored in the non-transitory computer readable medium and should be applied mutatis mutandis to method that may be executed by a computer that reads the instructions stored in the non-transitory computer readable medium.

The presently disclosed subject matter is directed to provide a system and method directed to evaluate the level of harassment of flying insects. Based on this evaluation, the presently disclosed subject matter enables measuring the actual number of insects within a flying insects' population, assessing the distribution of a given disease within an animal population, preventing disease, preventing adverse health conditions, improving animal welfare, and/or preventing nuisance.

Bearing this in mind, attention is drawn to FIG. 1, showing a schematic illustration of an environment in which the system for evaluating the level of harassment of flying insects on a plurality of animals in a given area (also interchangeably referred to herein as "system") operates, in accordance with the presently disclosed subject matter.

As shown in the schematic illustration, environment 100 includes an area 102 containing an animal population consisting of a plurality of animals 104 (e.g., livestock animals, domesticated animals, wild animals, and the like), and a flying insects' population consisting of a plurality of flying insects 106 (e.g., mosquitoes, flies (such as house flies, stable flies, blow flies, flesh flies, cluster flies, and the like), etc.) dispersed throughout the area 102, surrounding the plurality of animals 104. The dispersion of the plurality of flying insects 106 throughout the area 102 exposes the plurality of animals 104 to potential insect harassments and/or irritations, related diseases, and health conditions. As one example, area 102 may be a controlled environment configured to maintain optimal growing conditions throughout the development and/or life span of the plurality of animals 104 (e.g., a controlled pen, a controlled barn, and the like). As another example, area 102 may also be an uncontrolled environment (e.g., a meadow, a field, and the like).

The harassments and/or irritations may involve, for example, biting, stinging, blood sucking, and the like, and may cause the plurality of animals 104 to exhibit one or more insect repelling behaviors, such as ear movement (e.g., ear-flicking), head-shaking, legs stamping, tail swinging, and the like. The related diseases may involve, for example, Rift Valley fever, Trypanosomiasis, Blue-tongue, Ephemeral fever, Keratoconjunctivitis (pinky), Summer Mastitis, and the like.

Of the plurality of animals 104 found in area 102, one or more animals may each be associated with one or more components (e.g., an accelerometer, a gyroscope, etc.) and/or one or more systems (e.g., a vision system, etc.) capable of identifying and/or monitoring different types of ear movement patterns. For example, each of the one or more animals may have one or more accelerometers 108 (e.g., a micro-electromechanical system (MEMS) three-dimensional accelerometer or any other type of three-dimensional accelerometer) attached thereto. The three-dimensional accelerometers 108 can optionally be coupled to one or both ears of the animals in various manners. For example, in some cases, each of the three-dimensional accelerometers 108 can be a stand-alone device attached to the animal's ear/s, whereas in other cases, it can be part of an ear tag attached to the animal's ear/s. It is to be noted that the three-dimensional accelerometers 108 can be attached to the animal in other manners (e.g., as part of a neck monitoring tag attached to the animal by a collar), in which the placement of the accelerometers 108 enables determining movements of the ear/s of the animal to which they are attached.

Each given accelerometer unit of the one or more three-dimensional accelerometers 108 can be directed to detect one or more ear movement patterns associated with harassments and/or irritations caused by flying insects of the plurality of flying insects 106, as will be explained in further detail with respect to FIGS. 3 and 5. By way of example, an animal population consisting of a herd of nine dairy cows 104 is located at a controlled barn 102. Each of the nine dairy cows 104 has a three-dimensional accelerometer 108 coupled to its right ear and is surrounded by a plurality of stable flies 106 dispersed throughout the controlled barn 102. The respective three-dimensional accelerometer 108 of each dairy cow is aimed at detecting specific ear movement patterns of the cow's right ear, indicative of harassment and/or irritation caused by the plurality of stable flies 106.

Attention is now drawn to the components of the system for evaluating the level of harassment of flying insects on a plurality of animals in a given area 200.

FIG. 2 is a block diagram schematically illustrating one example of the system for evaluating the level of harassment of flying insects on a plurality of animals in a given area 200, in accordance with the presently disclosed subject matter.

In accordance with the presently disclosed subject matter, the system for evaluating the level of harassment of flying insects on a plurality of animals in a given area 200 (also interchangeably referred to herein as "system 200") can comprise a network interface 206. The network interface 206 (e.g., a network card, a Wi-Fi client, a Li-Fi client, 3G/4G client, or any other communication component) enables system 200 to communicate over a network with external systems and handles inbound and outbound communications from such systems. For example, system 200 can obtain ear movement patterns, ear movement pattern thresholds, and/or harassment thresholds, through network interface 206.

System 200 can further comprise or be otherwise associated with a data repository 204 (e.g., a database, a storage system, a memory including Read Only Memory—ROM, Random Access Memory—RAM, or any other type of memory, etc.) configured to store data. Some examples of data that can be stored in the data repository 204 include:

Ear movement patterns;

Ear movement pattern characteristics (e.g., ear movement rate, ear movement frequency, etc.);

Historical patterns;

Thresholds (e.g., harassment thresholds, ear movement rate threshold, pattern threshold, amplitude threshold, etc.);

Predefined rules;

Data associated with individuals (e.g., individual cows), groups of individuals (e.g., groups of cows);

Actions directed at reducing the level of flying insects at a given area; etc.

Data repository 204 can be further configured to enable retrieval and/or update and/or deletion of the stored data. It is to be noted that in some cases, data repository 204 can be distributed, while system 200 has access to the information stored thereon, e.g., via a wired or wireless network to which system 200 is able to connect (utilizing its network interface 206).

System 200 further comprises processing circuitry 202. Processing circuitry 202 can be one or more processing units (e.g., central processing units), microprocessors, microcontrollers (e.g., microcontroller units (MCUs)) or any other computing devices or modules, including multiple and/or parallel and/or distributed processing units, which are adapted to independently or cooperatively process data for controlling relevant system 200 resources and for enabling operations related to system's 200 resources.

The processing circuitry 202 comprises a harassment evaluation module 208 configured to perform a harassment evaluation process, as further detailed herein, inter alia, with reference to FIGS. 3 and 5.

Turning to FIG. 3, there is shown a flowchart illustrating one example of a sequence of operations carried out by the system for evaluating the level of harassment of flying insects on a plurality of animals in a given area 200, in accordance with the presently disclosed subject matter.

Accordingly, the system for evaluating the level of harassment of flying insects on a plurality of animals in a given area 200 can be configured to perform a harassment evaluation process 300, e.g., using the harassment evaluation module 208.

For this purpose, in accordance with and following the description referring to FIG. 1, the system for evaluating the level of harassment of flying insects on a plurality of animals in a given area 200 obtains one or more ear movement patterns (such as ear flapping, ear flicking, ear twisting, and the like) associated with at least one ear of at least one animal of the plurality of animals 104 (block 302). The one or more ear movement patterns may be determined by analyzing the three-dimensional accelerometer data acquired by the respective three-dimensional accelerometer/s 108 attached to the at least one ear of the at least one animal of the plurality of animals 104. For example, the three-dimensional accelerometer data acquired by each of the three-dimensional accelerometers 108 can be analyzed to identify a number of repetitions of events of abrupt change in ear acceleration over a set period of time. This number can then be compared to a predefined threshold, which serves as an indication of an ear movement pattern associated with harassment of flying insects, and once it is above the predefined threshold, the data can be obtained by the system 200. In a more specific example, in cases where the three-dimensional accelerometer is part of an ear tag coupled to an animal's ear, the repetitions of events of abrupt change can be so rapid, due to the constant ear movement, that the tag's sensors can become saturated and do not allow the tag's activity. These conditions were verified as being solely related to the presence of flying insects, through visual confirmation, which enabled the identification of the correlation between the events of sudden change and the presence of lying insects.

The one or more ear movement patterns may each be associated with its own characteristics, such as an ear movement rate as a function of time, and/or with characteristics common to all ear movement patterns (or a particular subgroup), which can be treated similarly.

Following the obtaining of the one or more ear movement patterns, system 200 determines, for at least part of the one or more ear movement patterns, whether their respective ear movement characteristics (e.g., ear movement rate) meet a predefined rule (e.g., exceeds an ear movement rate threshold, pattern threshold, amplitude threshold, follows a certain pattern over time, differs from historical patterns for an individual animal and/or group of animals, etc.) (block 304). The predefined rule can be defined, for example, by one or more of: (a) a comparison of the one or more ear movement patterns to empirical evidence of the amount of flies present, (b) use of historical patterns associated with the animals of the animal population, or group of animals of the animal population, (c) a comparison of the one or more ear movement patterns to norms arose from the system's 200 database, (d) an ability to correct the threshold/rule based on the time of day, weather, type of animal, geographic location climate, (e) use of external verification, such as visual confirmation (as mentioned therebefore), (f) use of other factors capable of empirically confirming an excess of flying insects, etc.

In cases where the predefined rule is based on a threshold, the threshold may be a definite value, a range of values, and the like, representing a level of irritation or harassment from which the inflicted irritation or harassment is considered to have a negative effect on milk yield, growth rate, etc.

System 200 then determines whether a number of ear movement patterns, whose characteristics met the predefined rule at block 304, meet an action requirement rule (block 306). The action requirement rule can be, for example, (a) the number of ear movement patterns whose characteristics met the predefined rule at block 304 is above a first harassment threshold (e.g., a definite value, a range of values, etc.), (b) a percentage of the number of ear movement patterns whose characteristics met the predefined rule at block 304 from a number of the plurality of animals is above a second harassment threshold (e.g., a percentage value), or (c) any other rule which enables determining that an action is required in order to reduce the level of harassment caused by the flying insects.

Figure 4A:
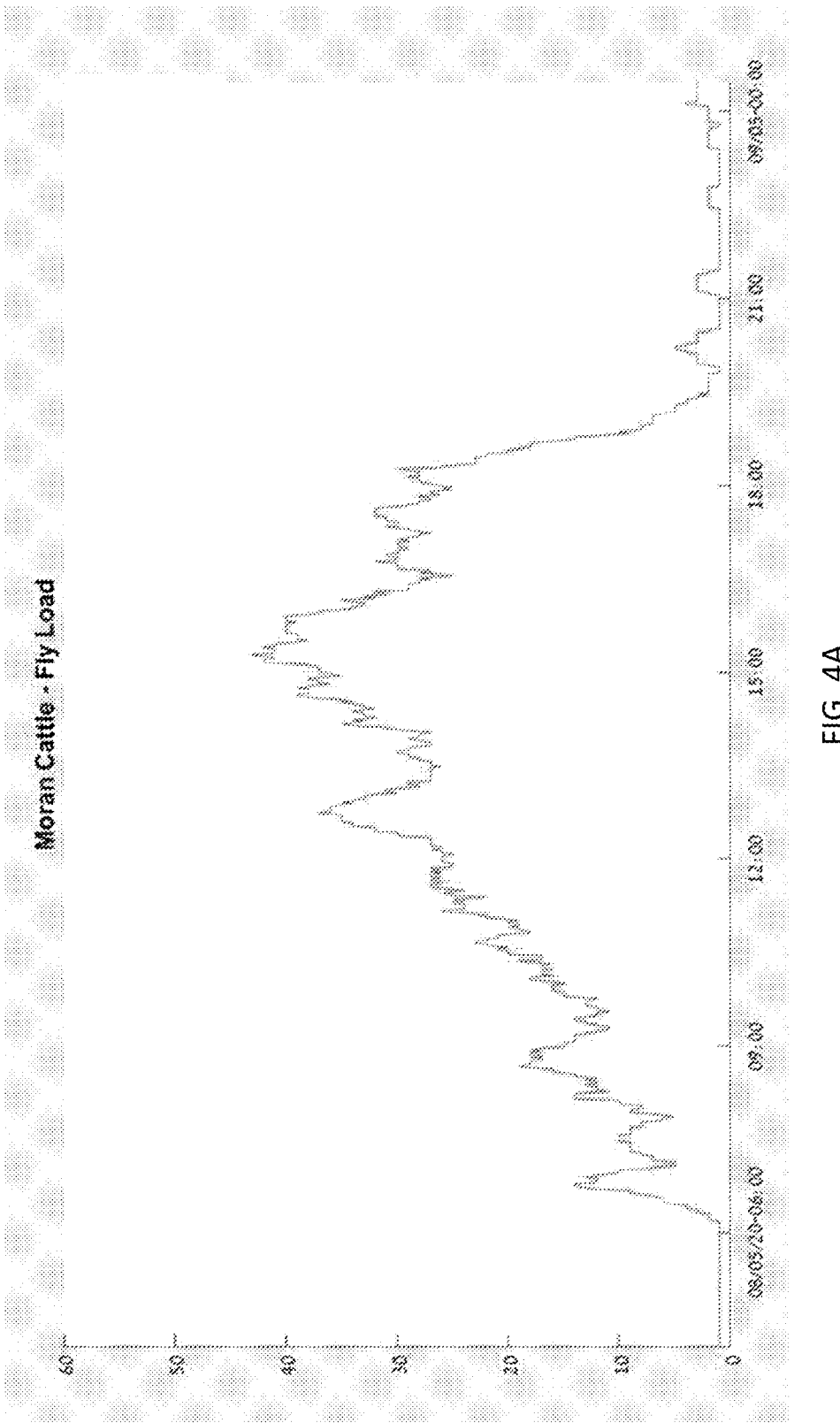
FIGS. 4A-4B are graphs of the percentage distribution of Moran cattle exhibiting an ear movement pattern having an ear movement rate that meets a predefined rule of ear movement rate, over a 24 hours period and an eleven days period, respectively, in accordance with the presently disclosed subject matter.
Figure 4B:
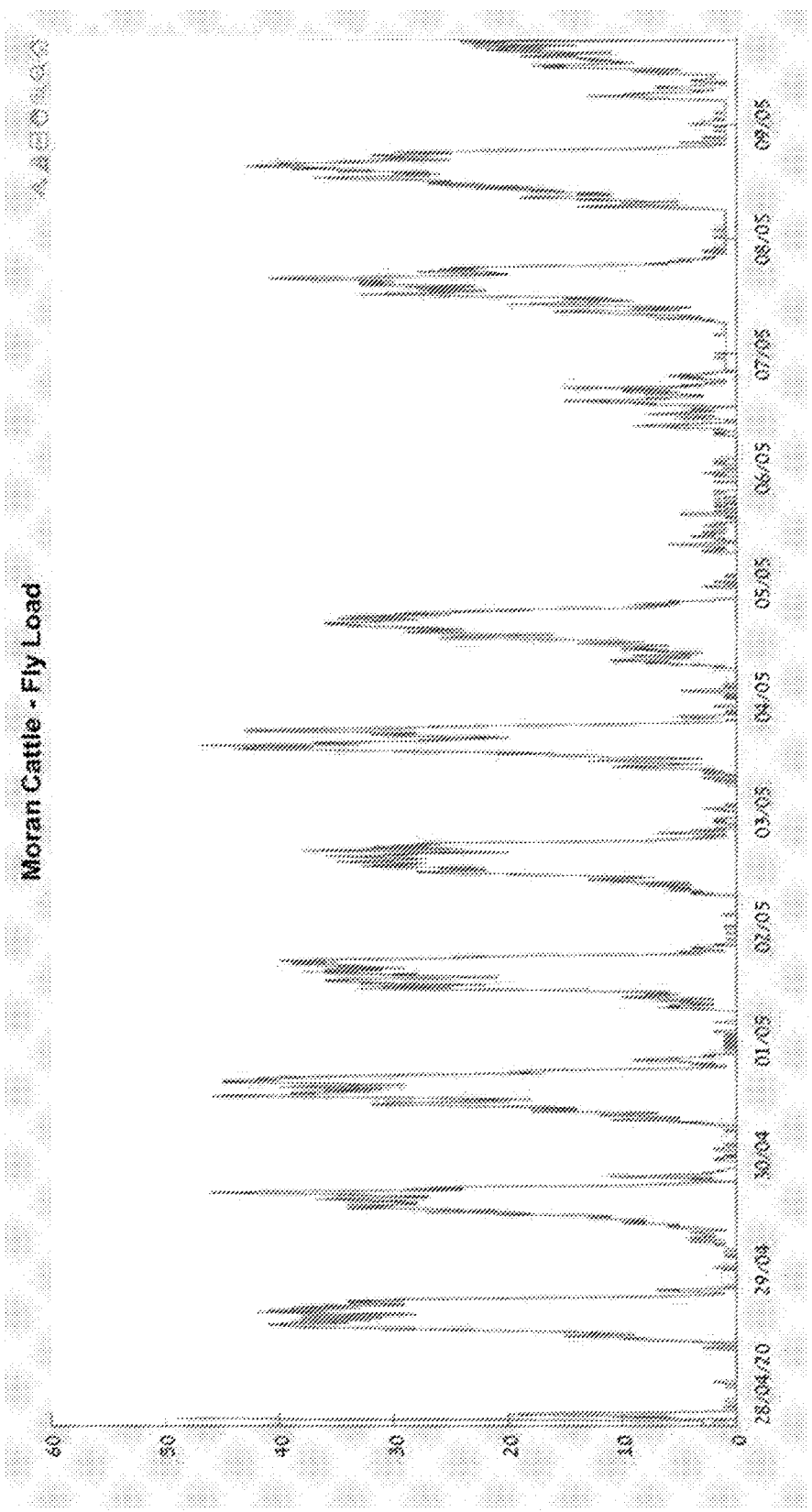

For example, FIGS. 4A and 4B are graphs of the percentage distribution of Moran cattle exhibiting an ear movement pattern having an ear movement rate that meets a predefined rule of ear movement rate, over a 24 hour period and eleven days period, respectively.

As illustrated in FIG. 4A, the percentage of Moran cattle exhibiting an ear movement pattern having an ear movement rate that meets the predefined rule is approximately zero between 00:00 and 06:00. This percentage rises between 06:00 and 15:00 (where it peaks at 40%) and drops between 15:00 and 19:30 until it reaches roughly zero percent at about 19:30, which is maintained until 00:00.

Turning the attention to FIG. 4B, which illustrates the percentage distribution of Moran cattle exhibiting an ear movement pattern having an ear movement rate that meets a predefined rule of ear movement rate, over 24 hours, along eleven straight days. As illustrated in the Fig., the percentage distribution of Moran cattle exhibiting an ear movement pattern having an ear movement rate that meets a predefined rule of ear movement rate, over 24 hours, remains constant in nine of the eleven days, while on the remaining two days (05/05 and 06/05) the percentage distribution is changed dramatically due to rain falling on both days (which is a known cause for a decrease in the number of flies).

In some cases, as demonstrated in FIG. 5, upon the action requirement rule being met, system 200 indicates that an action to reduce the number of flying insects at the given area is to be taken (block 308). The action may involve, for example, installing flying insects' papers, installing flying insects' traps, installing pesticide-releasing flying insects' strips, using repellent flying insects' sprays, using flying insects' predators, and the like. Alternatively, or additionally, system 200 can indicate that an action related to a given disease (e.g., checking for the presence of the disease and/or treating the disease, etc.) and/or an action directed to address a health condition of one or more animals of the animal population (e.g., providing tailored care, providing suitable medicine, etc.) is to be taken.

By way of example and in accordance with the example described herein in relation to FIG. 1, system 200 obtains the ear movement pattern of the right ear of each of the nine dairy cows 104, measured by the respective three-dimensional accelerometer 108 of each ear. The ear movement pattern of the right ear of each of the nine dairy cows 104 is associated with its own characteristic of ear movement rate as a function of time.

Of the nine dairy cows 104, the rate of the ear movement pattern of the right ear of four dairy cows is found to be 50 ear movements per minute, whereas the rate of the ear movement pattern of the right ear of the remaining five dairy cows is found to be 30 ear movements per minute. System 200 can then determine whether the ear movement rate of the ear movement pattern of the right ear of each of the nine dairy 104 cows surpasses an ear movement rate threshold of 40 ear movements per minute. Given that there are five right ears of five different dairy cows 104 having an ear movement pattern of 50 ear movements per minute, which surpasses the ear movement pattern threshold of ear movements per minute, the number of ear movement patterns surpassing the ear movement rate threshold is determined to be 5.

Following the determination of the number of ear movement patterns surpassing the ear movement rate threshold (5), system 200 can determine whether the percentage of the number of ear movement patterns surpassing the ear movement rate threshold from the nine dairy cows 104 is above a harassment threshold of 30%, as an example. As the percentage is above the threshold in this example, which is 55.55% (5 (dairy cows)/9 (total number of dairy cows)× 100=55.55%), is above the harassment threshold, system 200 sends an indication that an action involving installing stable flies' traps throughout the controlled barn's 102 area should take place.

It is to be noted that the reference in the example above is made to all types of movements (such as ear flapping, ear flicking, ear twisting, and the like) combined, however in other cases only a single type of movement or a selected sub-group of movement types can be considered. In these cases, alternatively or additionally to the use of accelerometers (e.g., a microelectromechanical system (MEMS) three-dimensional accelerometer or any other type of three-dimensional accelerometer), the system can utilize components, such as a gyroscope, etc., and/or methods, such as image processing, etc., to enable the identification of the type of ear movement.

It is to be further noted that any comparison of the ear movement rate with a threshold is a mere example and other types of rules can exist, such as pattern-based rules (e.g., an occurrence rate of various types of ear movements, trends in the rates of the ear movements, etc.).

It is to be further noted that in some cases, in addition to, or as an alternative for, the indication that an action is required in order to reduce the number of flying insects at the given area is to be taken, the system 200 can provide an indication of the level of harassment caused by the flying insects population. For example, an indication can be provided whether there is a low level of harassment, a medium level of harassment, or a high level of harassment caused to the animal population by the flying insects. As an alternative a numeral indication can be provided, indicating the level of harassment on a certain scale (e.g., 1-100). As another alternative, the raw data can be provided (e.g., how many animals demonstrate ear movement patterns which exceed a threshold, optionally indicating which specific animals, etc.).

In accordance with certain examples of the presently disclosed subject matter, system 200 can correlate the harassment level (that is determined as indicated hereinabove) with one or more other parameters associated with the animals, such as the animals' milk yield, the animals' feed intake, the animals' health, the animals' welfare (or components thereof, as further detailed hereinbelow), etc. In some cases, system 200 can use such correlations to set the rules used at block 304 and/or the action requirement rule of block 308, optionally dynamically (e.g., periodically). It is to be noted that in some cases different animal populations can have different harassment tolerances, so that having the ability to correlate the harassment level with other parameters as indicated herein can also enable determination of population specific rules for harassment levels.

As stated therebefore, in some cases, the evaluation of the harassment level disclosed therebefore can also be utilized by a welfare determination system, which will be described in detail hereafter, to determine the welfare of the animal population of the plurality of animals 104. The welfare can be determined by calculating a welfare score, as will be explained below, which may be affected by information obtained during the evaluation of the level of harassment, as will be clarified hereafter.

FIG. 6 is a schematic illustration of components of a welfare score for an animal population, in accordance with the presently disclosed subject matter.

Before turning to describe the figure, it is to be noted that the terms affectivity and happiness are used herein interchangeably with respect to the positive or negative effects of the environment on an animal population or part thereof and/or with respect to indications on the mental and/or emotional states of the animal population or part thereof.

Turning to the figure, in accordance with the schematic illustration shown therein, a welfare score for an animal population (or a part thereof) can be determined based on at least one of the following welfare Key Performance Indicators (KPIs): a health score 420, an affectivity/happiness score 430, and a natural living score 440. It is to be noted that the welfare KPIs can include additional or alternative elements directed to assist in determining the welfare score, such as an evaluation of a harassment level of flying insects, as described in relation to FIGS. 3 and 5. In cases where the harassment level is used to determine the welfare score, the score can be in inverse correlation with the level of harassment such that the higher the level of harassment, the lower the welfare score, and vice versa.

The calculation of the health score 420, the affectivity/ happiness score 430, and the natural living score 440 is based on data associated with members of the animal population. The data used for calculation of the welfare KPIs can be descriptive data (e.g., ages of the members, sex of the members, treatment history of the members, genetic information associated with the members, etc.) and/or monitoring data (e.g., parameters of the member of the animal population that are monitored over time using one or more monitoring devices, at least part of which can optionally be attached to the member), and/or data originating from other resources, as further detailed herein.

The monitoring data relating to each member of the animal population can include one or more of: location information (indicative of the geographical locations of the member), body temperature, respiration type, respiration levels, rumination time, movement type, movement time, feeding time, socialism time, elimination behaviors, internal rumen environment parameters (which can be monitored, for example, using a rumen bolus), etc.

The monitoring data can be obtained from sensors comprised within the monitoring devices, such as: one or more accelerometers, a temperature sensor, a location sensor (e.g., a Global Positioning System (GPS) receiver comprised within the monitoring device attached to the member), a thermal sensor, a pedometer, an animal identification component (e.g. an Identification (ID) Tag), a heart rate sensor, a biosensor, or any other sensor that can be used to monitor one or more parameters of the member of the animal population.

It is to be noted that in some cases, at least parts of the monitoring data can be measured over time. For example, rumination time, movement time, feeding time, socialism time, etc., can be the time from start to end of the respective activity. For example, if a member of the animal population started eating at 10:00 and finished eating at 10:30, the feeding time is 30 minutes. It is to be noted further that in some cases, at least parts of the monitoring data can be measured periodically, near continuously, or continuously, or in some combination (where some data is collected periodically and some data is collected continuously or near continuously). For example, body temperature, location, heart rate, etc. can be measured on a periodical basis (e.g., every minute, every 10 minutes, etc.), or continuously.

It is to be noted that whenever reference is made to continuously, near-continuously, real-time or near real time, the time intervals for obtaining a measurement can be milliseconds, seconds, minutes, hours or days, while noting that in comparison to current solutions in which human auditors are used, even time constants of days cannot be maintained, let alone time constants of hours, minutes, seconds or even less that are contemplated in accordance with the presently disclosed subject matter.

It is to be further noted that in some cases only parts of the data used for calculating the welfare score or components thereof are measured on a periodical basis (e.g., every minute, every 10 minutes, etc.), or continuously or near continuously, however due to the fact that each such newly acquired measurement can have an effect on the welfare score and/or components thereof, the welfare score and/or components thereof can be recalculated whenever new measurements are obtained, thus keeping the welfare score and/or components thereof updated in a similar periodical basis, or continuously or near continuously.

In some cases, at least some of the data relating to the member is extracted by analyzing optical information, e.g., images and/or videos, that include at least part of the member. Optical analysis can be used to determine the member's external impression, to assess the relationship between the member and its caregiver and even to determine the location of the member in relation to known landmarks in the image/video.

Utilization of the monitoring data allows for an objective, universal welfare assessment that can at least complement, if not replace, subjective human audits. In addition, utilization of the monitoring data can enable a real-time or near real-time automatic animal welfare assessment based on the collected monitoring data that can be collected in real-time or near real-time.

Monitoring devices gather at least some of the data relating to the animal population by monitoring the members' parameters over time. In some cases, at least part of the monitoring devices can be attached to a given member (e.g., in the form of a monitoring tag, a monitoring collar, etc.) thereby collecting (continuously, or near continuously, or periodically, or in some combination (where some data is collected periodically and some data is collected continuously or near continuously)) the given member's monitoring data.

Additionally, or alternatively, at least part of the monitoring devices may not be attached to a specific member, but be positioned in locations that allow for the monitoring of one or more members either simultaneously or sequentially. For example, at least part of the monitoring devices can be manual monitoring devices (operated by a human operator), stationary monitoring devices (e.g., monitoring members as they pass through a gate), autonomously driven monitoring devices (e.g., carried by autonomous drones), monitoring devices incorporated into a mobile device or into a computer, etc.

It is to be noted that at least part of the data gathered by the monitoring devices is associated with a respective member from which it was gathered. For this purpose, in some cases, at least some of the members of the animal population, and in some cases all members of the animal population, can have an identification (ID) means (such as, but not limited to, an ID tag such as an EID tag or a visual ID tag) attached thereto or otherwise associated therewith.

The ID means can be a tag that uniquely identifies the member of the animal population to which it is attached. In some cases, the ID means is part of a monitoring device attached to the member. However, the ID means may alternatively be another type of device used to identify the member using known and/or proprietary methods and/or techniques (including electronic identification, visual identification, camera-based identification, facial or body part recognition, barcode, identification marks, etc.).

As discussed, each member of the animal population can be identified using various systems/devices/methods/techniques, including an ID tag, identification marks (e.g., digits, letters, symbols, or any combination thereof, etc.), readable barcodes, facial (or other body parts) recognition, etc. When read by a suitable reading device (e.g., an ID tag reader), the ID means enables determining at least a unique animal identifier, uniquely identifying the member in question.

It is to be noted that in some cases, one or more of the identification methods may be passive identification methods, such as passive tags. For example, the tags can be a printing of a certain identifier on the animal to be identified, or they can be stickers of a certain visual identifier attached to the animal to be identified, or they can be markings painted on the animal to be identified. In such cases, where the tags are visually identifiable (e.g., barcodes), the respective tag reading device can be, for example, a camera capable of acquiring images in the spectrum of the visual tags.

The monitoring data gathered by the monitoring devices may be stored in records within a data repository. Each record may be associated with a respective member of the animal population and can contain different types of data, including descriptive data, monitoring data, a combination of descriptive data and monitored data, and optionally other types of data.

For example, a record may contain (a) descriptive data (e.g., age of the respective member, sex of the respective member, treatment history of the respective member, genetic information associated with the respective member, etc.) that was not necessarily gathered by the monitoring devices, and (b) monitoring data (e.g. a body temperature of the respective member, movement time of the respective member, feeding time of the respective member, socialism time of the respective member, respiration levels of the respective member, rumination time of the respective member, etc.).

As indicated above, such monitoring data can be monitored continuously, or near continuously, or periodically, or in some combination (where some data is collected periodically and some data is collected continuously or near continuously), using the monitoring devices. Accordingly, when the monitoring data is monitored in a continuous, near continuous, or periodical manner, or in some combination (where some data is collected periodically and some data is collected continuously or near continuously), the respective records can be updated accordingly (e.g., by updating an existing record associated with the respective member, or by adding an additional record indicating the newly acquired values). In some cases, the updating of at least some of the parameters forming a record associated with a respective member can be by averaging the values of the respective parameter/s over time or by performing any mathematical and/or statistical calculation thereon.

Attention is now drawn to the calculation of health score 420 for a given member of the animal population, which can form part of the welfare score calculation, as indicated herein. The health score 420 for a given member of the animal population is determined based on criteria of basic health and functioning of the given member, including, specifically, freedom from disease and injury. In some embodiments, health score 420 can be calculated based, at least in part, on identifying symptoms that can be associated with health-related issues (e.g., illness, injury, etc.). In some cases, the health score 420 is determined based on finding statistically significant correlations between the identified symptoms and illnesses or injuries. In some cases, the strengths of such correlations between the symptoms that are indicative of illness and/or injuries is also used in order to determine the health score 420.

Those symptoms can be identified by monitoring rumination and/or energy levels of an individual member, of a group of members of the animal population or, of the entire animal population. Additionally, or alternatively, the symptoms can be identified by based, at least in part, on monitoring visual indicators associated with health problems and/or monitoring breathing patterns of an individual member, of a group of members of the animal population or, of the entire animal population.

Energy level can be measured, for example, by detecting movements of a given member over a given time period (e.g., a day) and deducing the amount of energy required from the given member to perform these movements (optionally based on specific characteristics of the given animal). The movements can be detected by monitoring an acceleration signal obtained for example from an accelerometer comprised within a monitoring device attached to the given member.

Rumination can be measured, for example, by detecting ruminating activity of a given member over a given time period (e.g., a day). This can be achieved by analyzing acceleration signal obtained for example from an accelerometer comprised within a monitoring device attached to the given member and detecting signals that correlate to reference signals that are known to be associated with rumination activity.

Breathing patterns can be determined, for example, by detecting various breathing patterns of a given member over a given time period (e.g., a day). This can be achieved by analyzing acceleration signal obtained for example from an accelerometer comprised within a monitoring device attached to the given member and detecting signals that correlate to reference signals that are known to be associated with specific breathing patterns. This can enable determining whether the given animal demonstrates suspicious behavior (e.g., if it is breathing heavily more than usual and/or over a predetermined threshold, etc.).

Visual indicators associated with health problems can be identified using image analysis of images and/or videos of the members of the animal population. For example, scratching or irritation that are correlated with morbidity symptoms can be identified using image and/or video analysis.

It is to be noted that these are mere examples for determination of symptoms that can be associated with health-related issues, and additional and/or alternative data can be used to determine the above indicated symptoms, or other symptoms that can be associated with health-related issues.

The health score 420 of the members of the animal population can be used for calculating a health index indicative of the overall health level of the members of the animal population. In some cases, the health index can be used for identifying morbidity levels in the animal population. For example, a health index showing that more than a threshold (e.g., around 5%) of the animals in the animal population are having health scores 420 below a threshold can be an indication of a developing health problem within the animal population. A health index showing that more than a second threshold (e.g., around 10%) of the animal population are having health scores 420 below a threshold can be an indication of a prevailing health problem. A health index showing that more than a third threshold (e.g., around 20%) of the animal population are having health scores 420 below a threshold can be indicative of a pandemic.

It is to be noted that analysis of the health scores 420 can enable identification of given animals of the animal population that have a certain health issue (e.g., illness, lameness, estrus, etc.). In some cases, analysis of the health index (generated based on the health scores 420 of the members of the animal population) can enable, at the population level, identifying whether the overall health level of the animal population is above an acceptable predetermined health threshold.

Attention is now drawn to the calculation of affectivity/happiness score 430 for a given member of the animal population. The calculation of affectivity/happiness score 430 for a given member of the animal population can be based on a state the given member is in, for example: pain, distress, frustration, pleasure, etc. Affectivity/happiness score 430 can reflect how the given animal is affected by its environment and its experiences (is it positively affected by its environment or negatively affected by its environment). In some cases, the calculation of affectivity/happiness score 430 for a given member of the animal population is based on level of suffering of the given animal, so that the more suffering is identified—the lower its affectivity/happiness score 430 is.

The state of the given member, or its level of suffering, can be determined, for example, based on changes in its breathing patterns, its rumination activity, its eating activity, or some combination thereof. For example: measuring the variability of rumination and eating times, and levels of heavy breathing between members of an animal population, optionally on a daily basis, can provide a basis for the affectivity/happiness score 430.

One specific exemplary measure based on which the affectivity/happiness score 430 can be determined is the consistency of Rumination Variability (RV) for a period of ten days within the animal population. This analysis indicates that reduced ration digestibility can result in increased risk for metabolic issues and decreasing consistency and that optimal intake will be reflected by consistent, low levels of RV.

Another measure based on which the affectivity/happiness score 430 can be determined is heavy breathing. Analysis of the breathing levels of members of the animal population indicates that heavy breathing is indicative of heat stress (discomfort). It is to be noted that when analyzing heavy breathing behavior on a group level, increased heavy breathing implies overall heat stress amongst the animals in the animal population.

One non-limiting exemplary situation that impacts the affectivity/happiness score 430 for a population of ruminating animals includes increased competition between a given group of members of the ruminating animals population (for example: as a result of lack of bunk space resulting in increased competition for food) that will result in higher variability of rumination and eating times between the members of the given group and will result in a lower affectivity/happiness score 430 for that group of members of the ruminating animals.

Additional examples of circumstances that impact affectivity/happiness score 430 are: bedding conditions of members of the animals population, lighting conditions, square feet per meter per member of the animal population (so as not to overstock the animals), water and feed availability (for example: queuing in front of the water trough is a sign that not all the members of the animal population receive their needs), results of spectrographs of milk of the members of the animal population (for milk giving animals), image analysis of feed and feeding area, feed that is taken only by the more dominant members of the animal population can suggest an issue with levels of feed provided and/or a social problem between the members of the animal population.

In some cases, problems may be inferred from the affectivity/happiness score 430. For example, finding inconsistencies or increasing differences between the members of the animal population in an affectivity/happiness score 430 that is based on the housing conditions for the animals may lead to a conclusion that there is a problem in the bedding conditions (which is part of the housing conditions) for these members.

Turning to the natural living score 440, the calculation thereof is based on analysis of behaviors indicative of the ability of the given animal to live a reasonably natural life by carrying out natural behavior and having access to natural elements in its environment. These specific behaviors can include: eating activity, grazing activity, activity level (e.g., the quantity and intensity of movement of the given animal), walking activity, etc. These behaviors can be used to verify that animals have, for example, enough time and opportunity to eat, express normal high-levels of activity, are not forced to walk to much, or are restricted from appropriate amounts of movement/walking. A non-limiting example related to the natural living behavior for dairy cows is in a dairy farm wherein calves may be regularly separated from their mothers within the first day after birth, and are fed milk from a bucket, usually twice per day. With such infrequent meals the total milk intake is limited so that the calf does not receive too much milk at one time. By contrast, under natural conditions, cows stay fairly close to the calves for the first two weeks, and the calf will feed many times per day in smaller meals. Adjusting the feeding systems to correspond more closely to the animals' natural behavior (staying close to the mother and feeding often but in relatively smaller amounts) will result in a higher natural living score 440 for that calf. An additional example related to the natural living behavior is the time spent by a grazing animal in the pasture looking for food that can suggest a need for fencing reallocation.

As further detailed herein, A single welfare KPI (e.g., one of the: health score 420, affectivity/happiness score 430 or natural living score 440), or any combination of welfare KPIs, can be utilized to determine the welfare of the animal population, or of a sub-group within the population, or of a single member of the animal population and optionally to suggest an action to be taken upon the member/s of the animal population. Such actions can include treating the member(s), moving the member(s), examining the member(s), separating the member(s) from the remainder of the animal population, changing the feeding conditions of at least some of the members, changing the water conditions of at least some of the members, changing the bedding conditions of at least some of the members, etc.

Automatic determination of the welfare of members of an animal population, using the teachings herein, can enable calculating a welfare score without the need for presence of a human auditor, and in time intervals that are impossible for a human operator (and optionally even in real time or near real-time). The welfare KPI scores can also take into account large amounts of data, including historical trends, whereas human auditing is limited in the human's ability to gather and obtain insights from large amounts of data. Still further, due to the fact that the welfare KPIs score determination is not made by humans it does not suffer from human bias. Personal impression and auditing proficiency have no effect on the automatic welfare KPIs score determination in accordance with the teachings herein. It is to be noted that in some cases, audits are made on a six-monthly basis, or even in longer time intervals, and clearly in such situations issues may arise that will simply be unnoticed and unassessed for six months.

The automatic determination of animal welfare disclosed herein can also be used to improve the wellbeing of a given animal or groups of animals of the animal population in real time, or near real time. For example, the system and method disclosed herein can enable identifying declining animal conditions of a single animal or a group of animals of the animal population. Further, the system and method disclosed herein can provide the animal caregiver and/or a regulator (such as a governmental organization) with information that can be used to take action in real or near real time to improve animal welfare, such as by obtaining treatments for veterinary or health issues such as: infectious diseases, ectoparasites, and/or reproductive issues.

Moreover, based on the system and method disclosed herein, benchmarks can be determined for one or more locations or facilities of animal populations. These benchmarks can be used as references over time to automatically determine the adherence of the facilities or locations with an expected level of animal welfare. These benchmarks can be measured and adjusted, optionally continuously.

Still further, the system and method disclosed herein can utilize objective, automatic and optionally continuously, collected information to empirically determine welfare scores that can enhance or replace the traditional human auditing method of animal welfare. By that, the system and method disclosed herein can provide a non-biased, fraud-free, universal model for evaluating animal welfare.

The animal welfare disclosed herein can be used to set standards (optionally industry wide standards), benchmark between different animal populations and/or between groups of members of one or more animal populations, and provide management or veterinarian support, optionally in real time, to mitigate and reduce emerging risks. The animal welfare disclosed herein can also be used by insurance and/or finance providers to evaluate risks in insuring and/or financing related to the animal population.

For example, the animal welfare (including the animal welfare KPI scores) disclosed herein can be used to set standards for minimal animal welfare for various types of animal caregivers, whether institutional (such as farms in which cows, swine, equine or any other type of animal is maintained, for slaughter, milk production or for any other purpose) or private animal owners (such as pet owners). Having such standards can enable regulation (enabling governments or other regulators make sure that animal welfare meets the required standards, and quickly identify any irregularity), value and/or risk estimation (enabling insurers, lenders or other type of financial institutions, trade associations, customers, or any other entity that is interested in valuation and/or risk estimation of the animals or their products, to more accurately evaluate the animals or their products such as milk, meat, etc.), and more. For example, the improved objectivity, consistency, frequency, and reliability of the welfare systems and methods descried herein allows for more accurate and precise comparison between disparate farms/animal facilities, which is one of the advantages that enables entities to generate effective standard setting, risk estimation regulation, etc.

In some cases, the animal welfare score can also be used as a measure based on which a certification of animal welfare can be provided, similarly to the Marine Stewardship Council (MSC) Certification used in the fishing industry.

It is to be noted that the ability of the system disclosed herein to monitor the animal welfare (utilizing the animal welfare KPI scores) of animal populations in a continuous (or near continuous) reliable, consistent, and objective manner, is extremely powerful and important. The monitoring described herein enables all stakeholders (animal caregivers, regulators, financial institutions, trade associations, milk processors, meat processors, retail chains, end-customers, or any other entity that may have an interest in the animals' welfare) to receive relevant information for making decisions in real-time, or almost in real-time (e.g., within milliseconds, seconds, minutes, hours or days) based on continuously, or near continuously, updated reliable, consistent, and objective information (as opposed to existing solutions in which such information is unavailable). A few non-limiting examples for uses of the animal welfare according with the presently disclosed subject matter: financial institutions can evaluate risks based on relevant information indicative of the animal welfare at the time they make decisions; Regulators can act upon detecting an irregularity when the irregular situation is detected and not in retrospect; retail chains, milk processors, meat processors, end-customers, or any other consumers of products of the animal population can get information of the animal welfare of the animal population from which the products originate; veterinarians can proactively act upon an identified need based on the animal welfare; diary and/or meat producers can compare farms based on the animal welfare, so they can make informed purchasing decisions.

In some cases, the welfare score can be determined also based on a sustainability index and/or based on a greenhouse gases index. In such cases, the information based on which such index/es are determined can be obtained using sensors that gather relevant information (e.g., water and/or energy resources use, waste generation, freshwater use, air gases, etc.).

It is important to note that the welfare score according to the teachings herein is determined based, at least in part, on direct analysis of the animals behavioural and physiological signals and not based on human interpretation.

Figure 9:
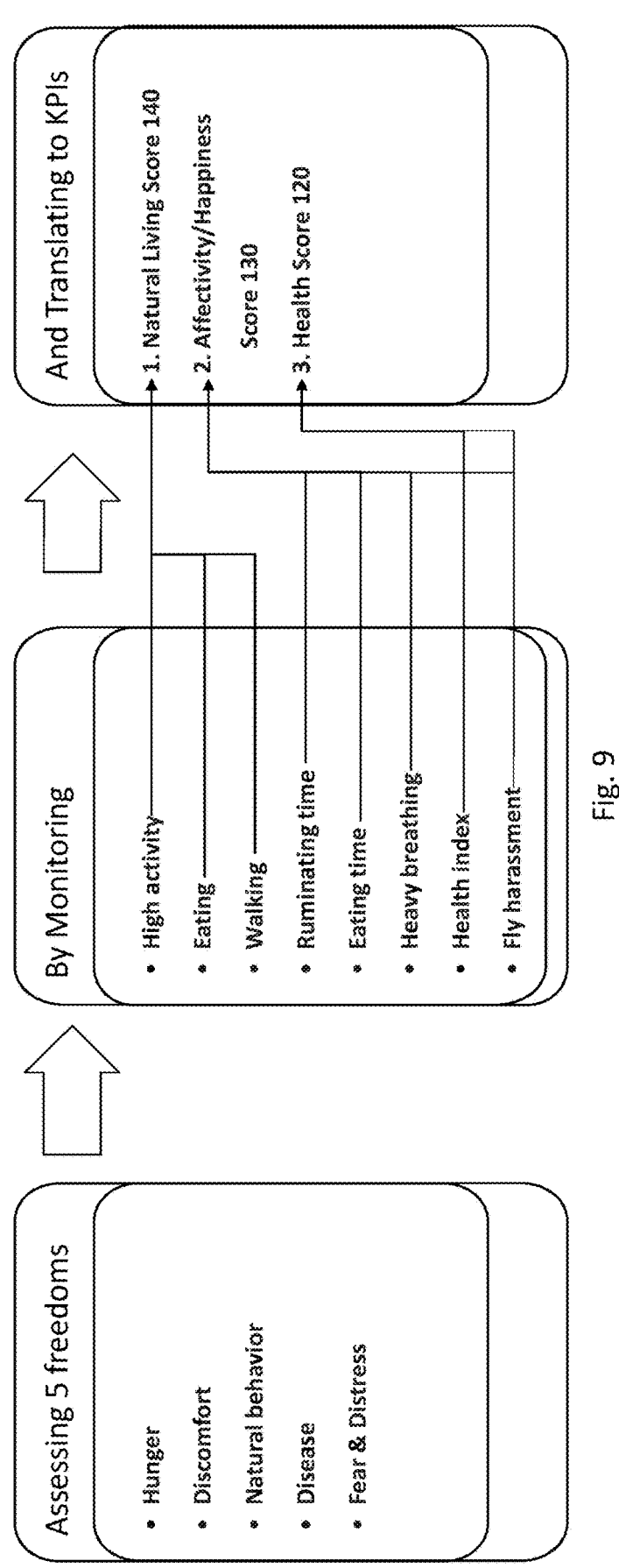
FIG. 9 is a schematic illustration of the determination of welfare KPI scores for an animal population, in accordance with the presently disclosed subject matter.

A schematic illustration of a non-limiting example of determining welfare KPI scores for an animal population can be viewed in FIG. 9, wherein the assessment of freedoms of the animal population is achieved by continuously gathering the monitoring data and the descriptive data (as detailed herein) associated with the animal population. The welfare KPI scores are determined based on the gathered data.

It is to be noted that the monitoring data types examples in FIG. 9 are non-limiting examples and that the types of monitoring data may vary for different types of animal population. For example: for companion animals the data that is monitored can include play behavior, socializing with other animals, etc. For livestock the data monitored can include activity level, eating time, walking time, rumination time, heavy breathing, health-related parameters (e.g., body temperature, etc.) living conditions, stock levels, feed time behavior, play behavior, socializing with other animals, fly harassment (e.g., determined by ear movement pattern/s), etc.

It is to be further noted that companion animals' welfare is viewed more on the individual animal level, while livestock welfare is viewed more on the population level.

In some cases, the animal population can be located at one or more facilities (e.g., farms, enclosures, etc.). In such cases, a welfare score can be calculated on a facility level, by analyzing the welfare KPI scores associated with the members of the animal population located in that facility. For example, different farms can have their own welfare scores allowing comparison between farms.

In addition, the welfare KPI scores can be used to monitor the wellbeing of groups of members of the animal population, thus giving tools to the human care giver of the animals to monitor as well as more economically manage the animal population over time. The welfare KPI scores described herein have many benefits for the animals and the animal care givers. For example, animal management can use the welfare KPI scores internally, for example within a farm, by moving specific members or groups of members between enclosures within the farm, thus achieving hierarchy balancing by managing and removing feeding and social pressure from individual animals or from groups of animals). As indicated herein, the welfare KPI scores can also provide reliable, objective, consistent, and continuous information to all stakeholders (animal caregivers, regulators, financial institutions, trade associations, milk processors, meat processors, retail chains, end-customers, or any other entity that may have an interest in the animals' welfare) for decision making.

As a non-limiting example of utilizing the welfare KPI scores, the scores can help an animal care giver maintains his farm's sustainability by identifying the specific operation segment that requires attention, for example: bedding, feeding, milking, treatment, or any other segment of a farm. The animal care giver in this non-limiting example can monitor overall morbidity of the animal population, observe members that are breaking down due to being pushed beyond their metabolic capacity or being poorly-managed, which may affect their production efficiency and prevent them from reaching their optimal production capacity. The animal care giver can also examine housing conditions, identify historical trends within the animal population and create benchmarks that are continuously measured and adjusted for his farm. The benchmarks can be on the animal welfare score and/or on any one, or any combination of the health score 420, the affectivity/happiness score 430, or the natural living score 440, and, as indicated herein, any one of the benchmarks, or any combination of two or more of the benchmarks can be updated manually, or automatically.

The welfare KPIs can be also used by regulation entities or sourcing companies for monitoring regulated or supplier farms, develop procedures with the animal care giver they regulate or source from, manage public and customer opinion and ensure they maintain transparency around their brand name and brand value.

In addition, the welfare KPI scores can be used to improve the overall health of a given member of the animal population, or groups of animals of the animal population, by identifying a condition and suggesting treatments for veterinary issues even before external indications of illness are detected. As some animals do not externalize sickness symptoms, the welfare KPI can express a change in the animal population that is suggestive of a health problem of some of the members of the animal population. This can enable earlier and more effective treatment of health problems—for example by saving on more invasive drugs and treatments; by starting treatment earlier due to an earlier alert compared to other methods, and this in turn will reduce the number of sick animals, reducing the length of time the animal population is impacted by any health problems, etc. The early recognition of problems can also prevent changes to the member's routine that can lead to discomfort to the member of the animal population. A routine (e.g., feeding times, activity periods, rumination and social behavior schedules, etc.) of a single member and/or a group of members and/or the entire animal population can be identified by analyzing the welfare KPI scores during a specific time period. Once a consistent routine is identified, changes in the welfare KPI scores can be used to identify early warning signs of alterations in the consistent routine before a collapse of that routine.

For example, if a given group of members of an animal population has a health score 420 below a specific threshold (for example: a health score 420 that indicates a percentage of sick members of the animal population is greater or equal to 10% of the population) and a natural living score 440 below a second threshold (for example: the recorded feed availability and/or walking distance covered during the day and/or high activity levels are a threshold percentage over or under historical levels), this measurement can be indicative of an infectious disease problem within the population (e.g., respiratory diseases, gastro-intestinal diseases or reproductive diseases).

These infectious diseases for cows can include, for example, one or more of: respiratory diseases where the pathogens involved are bacteria, among others: *Mannheimia haemolytica, Pasteurella multocida, Mycoplasma bovis*, and *Histophilus somni*; and viruses, amongst others: bovine coronavirus (BCV), parainfluenza-3 (PI3) virus, bovine respiratory syncytial virus (BRSV), bovine viral diarrhoea virus (BVDV) and bovine herpes virus 1 (BHV1), which causes infectious bovine rhinotracheitis (IBR).

Genera diseases, where additional immunoactive components are based on, or derived from, micro-organisms that are pathogenic to ruminants. Examples of such microorganisms are: for bovines (the bovine animal is taurine cattle (*Bos taurus*), zebu cattle (*Bos indicus*), buffalo, bison, yak, or wisent): *Neospora* spec., *Dictyocaulus* spec., *Cryptosporidium* spec., *Ostertagia* spec., bovine rotavirus, bovine viral diarrhoea virus, bovine coronavirus, infectious bovine rhinotracheitis virus (bovine herpes virus 1), bovine paramyxo virus, bovine parainfluenza virus, bovine respiratory syncytial virus, rabies virus, bluetongue virus, *E. coli, Salmonella* spec., *Staphylococcus* spec., *Mycobacterium* spec., *Trueperella* spec., *Brucella* spec., *Clostridia* spec., *Pasteurella* spec., *Mannheimia* spec., *Haemophilus* spec., *Leptospira* spec., and *Fusobacterium* spec., *Mycobacterium bovis*, and *Trueperella pyogenes*. For sheep and goats (caprine, ovine): *Toxoplasma gondii*, peste des petit ruminant virus, bluetongue virus, Schmallenberg virus, *Mycobacterium* spec., *Brucella* spec., *Clostridia* spec., *Coxiella* spec., *E. coli, Chlamydia* spec., *Clostridia* spec., *Pasteurella* spec., and *Mannheimia* spec. For cervines: Epizootic haemorrhagic disease virus, bluetongue virus, papilloma virus, *Borrelia burgdorferi, Mycobacterium bovis*, and *Trueperella pyogenes*. Reproductive diseases such as: Mastitis: Staph and Strep, fertility metritis: *Trueperella pyogenes, E. coli*, and *Fusobact. necrophorum*.

The infectious diseases of swine can include, for example, one or more of enteric pathogens which include *Salmonella* spp., in particular *S. typhimurium, S. choleraesuis*; Lawsonia intracellularis; Astroviruses; Rotavirus; Transmissible gastroenteritis virus; *Brachyspira* spp, in particular *B. hyodysenteriae, B. pilosicoli; Clostridium* spp., in particular *C. difficile, C. perfringens* types A, B and C, *C. novyi, C. septicum, C. tetani*; Porcine enteric picornaviruses; Porcine enteric caliciviruses; respiratory pathogens, which include: *Actinobacillus pleuropneumonia; Bordetella bronchiseptica; Erysipelothrix rhsiopathiae; Haemophilus parasuis*, in particular subtypes 1, 7 and 14; *Pasteurella* spp., in particular *P. multocida; Mycoplasma* spp., in particular *M. hyopneumoniae, M. hyorhinis*; Swine influenza virus; PRRS virus; PED virus; Porcine circovirus, in particular PCV2 and PCV3; Porcine parvovirus; Pseudorabies virus; Eperythrozoonosis suis, *Mycobacterium* spp., in particular *M. avium, M. intracellulare, M. bovis*; Porcine respiratory corona virus; Arcanobacterium *pyogenes*; Porcine adenovirus; Classical swine fever; Porcine cytomegalovirus; African swine fever virus; or other pathogens, which include *Escherichia coli, Streptococcus* spp., in particular *S. suis, S. porcinus, S. dysgalactiae*, preferably subsp. *equisimilis; Brucella suis*, in particular biovars 1, 2 and 3; *Leptospira* spp., in particular *L. australis, L. canicola, L. grippotyphosa, L. pomona, L. icterohaemorrhagicae, L. interrogans, L. tarassovi, L. hardjo, L. sejroe*; Encephalomyocarditis virus; Hemagglutinating encephalomyelitis virus; Japanese encephalitis virus; West Nile virus; Reovirus; Rubulavirus; Menangle virus; Nipah virus; Vesicular stomatitis virus; Virus of vesicular exanthema of swine; Swine pox virus; Swine herpes virus; and *Staphylococcus hyicus*.

An action can then be taken, for example, to treat the situation, as further detailed herein, inter alia with reference to FIG. 8. An action can be suggested based on the overall welfare score and/or the health score 420, and/or the affectivity/happiness score 430 and/or the natural score 440 of the animals within the population.

Having described the components of the welfare score, attention is now drawn to FIG. 7. FIG. 7 is a block diagram schematically illustrating one example of a welfare determination system for determining the welfare of an animal population, in accordance with the presently disclosed subject matter.

Welfare determination system 500 comprises a network interface 520 (e.g., a network card, a WiFi client, a LiFi client, 3G/4G client, or any other component), enabling Welfare determination system 500 to communicate over a network with external systems from which it obtains monitored parameters of members of an animal population and/or descriptive data associated with the members. The external systems can be monitoring devices configured to monitor parameters of the members, or any other intermediate system(s) that obtain the information about the members from the monitoring devices (e.g., computerized systems that manage at least part of the members of the animal population).

Welfare determination system 500 further comprises, or is otherwise associated with, a data repository 510 (e.g., a database, a storage system, a memory including Read Only Memory—ROM, Random Access Memory—RAM, or any other type of memory, etc.) configured to store data, optionally including, inter alia, animal information records. Each information record is associated with a distinct member of the animal population and can include descriptive data of the member (e.g., age of the distinct member, sex of the distinct member, treatment history of the distinct member, genetic information associated with the distinct member, etc.) and monitoring data and/or monitored parameters of the distinct member as monitored by the monitoring devices over time (e.g., health parameters, behavioral parameters, affectivity/happiness parameters, etc.). Data repository 510 can be further configured to enable retrieval and/or update and/or deletion of the stored data. It is to be noted that in some cases, data repository 510 can be distributed, while the Welfare determination system 500 has access to the information stored thereon, e.g., via a wired or wireless network to which Welfare determination system 500 is able to connect (utilizing its network interface 520).

Welfare determination system 500 further comprises a processing circuitry 530. Processing circuitry 530 can be one or more processing units (e.g., central processing units), microprocessors, microcontrollers (e.g., microcontroller units (MCUs)) or any other computing devices or modules, including multiple and/or parallel and/or distributed processing units, which are adapted to independently or cooperatively process data for controlling relevant Welfare determination system 500 resources and for enabling operations related to Welfare determination system's 500 resources.

Processing circuitry 530 can comprise a Welfare KPIs determination module 540. Welfare KPIs determination module 540, can be configured to determine the welfare KPIs for an animal population (or a group within that population), as further detailed herein, inter alia with reference to FIG. 8.

Turning to FIG. 8, there is shown a flowchart illustrating one example of a sequence of operations carried out for determining the welfare of an animal population, in accordance with the presently disclosed subject matter.

In accordance with the presently disclosed subject matter, Welfare determination system 500 can be configured to perform welfare KPIs determination process 600 (optionally in real-time or near-real time), e.g., using Welfare KPIs determination module 540.

As indicated herein, with reference to FIG. 6, the welfare KPIs are determined based on data associated with members of the animal population. The data can originate from various sources, from within the system and/or from external systems. For example: some of the data can be descriptive data (e.g., age of the distinct member, sex of the distinct member, treatment history of the distinct member, genetic information associated with the distinct member, etc.) and some of the data can be monitoring data, e.g., parameters of the animal (for example: temperature, movement time, feeding time, social behavior time, respiration levels, rumination time, etc.) that are monitored over time using one or more monitoring devices.

The data gathered from the monitoring devices is stored in records within a data repository. Each record is associated with a respective member of the animal population and holds descriptive data (e.g., age of the respective member, sex of the respective member, treatment history of the respective member, genetic information associated with the respective member, etc.) and monitoring data, e.g., parameters of the animal (for example: temperature, movement time, feeding time, social behavior time, respiration levels, rumination time, etc.) obtained from the monitoring devices. Monitoring data may be collected continuously, or near continuously, or periodically, or in some combination (where some data is collected periodically and some data is collected continuously or near continuously).

Welfare determination system 500 is configured to obtain at least a subset of the records, the subset being associated with a first group of members of the animal population (block 610). In some cases, all of the records of the animal population are obtained by Welfare determination system 500. In other cases, the first group of members can consist of a sub-population of the animal population, selected in accordance with one or more criteria (e.g., sex, age, location, treatment history, etc.). For example: the animal population can be dairy cows within a given farm and the sub-population are all the dairy cows that received a given treatment during the last year. It is to be noted that the animal population can be located in one or more geographical sites and/or within specific locations within these sites (e.g., enclosures, pasture, treatment areas, etc.).

The animals of the animal population can be for example: ruminating animals, livestock, swine, companion animals or any other type of non-human animal.

After obtaining the at least subset of the records, Welfare determination system 500 is further configured to calculate, based on the subset of records, for at least part of the members of the first group of members, at least one of: (a) a health score 420 indicative of a health state of the respective member, (b) a natural living score 440, indicative of compliance of a behavior pattern of the respective member with a desired natural behavior pattern, or (c) an affectivity/happiness score 430, indicative of compliance of an affectivity/happiness measure of the respective member with a desired affectivity/happiness measure (block 620).

For the health score 420 calculation, the parameters that can be used can include, for example, the energy level of the given member and/or the time the given member ruminates. Rumination, energy levels, heavy breathing, chewing, core temperature, Image analysis to identify indicators of health problems and optionally additional and/or alternative indicators from the member can determine if the member has health disorders (e.g., illness and/or injury, etc.). The health score 420 calculation can be based on the absolute values of these parameters, on changes of these monitored parameters over time, relative values of these parameters (such as percentages, etc.) or on a combination thereof.

The health score 420 for the given member can be determined, for example, based on the consistency of the values of at least some of the parameters over time (e.g., their consistency over a rolling average for a given time period, such as a ten-day rolling average). In some cases, the consistency of the values can be measured against reference parameters, for example: reference parameters that are measured from reference animals. Actual members of the animal population (other than the given member) or from another population can be used as reference animals. Historical data can also be used as reference. In some cases, the reference can be a theoretical reference of how a hypothetical reference animal should behave.

For the affectivity/happiness score 430 calculation, the parameters that can be used for the calculation can include, for example, one or more of: (a) respiration activity, including respiration level of the given member (e.g., level of respiration suggestive of a panting animal, or heavy breathing) (b) rumination activity, including percentage of rumination time for the given member within a given time period, for example: the time a given member has ruminated during a given time period (e.g. a day), (c) feeding activity, including percentage of feeding time for the given member within a certain time period, for example: the time a given member was feeding during a given time period (e.g. a day), or (d) external impression of the given member (e.g., using automatic image analysis of images and/or videos that include at least part of the given member).

The affectivity/happiness score 430 calculation can be based on the values of these parameters and/or on changes in the values of these monitored parameters over time. The affectivity/happiness score 430 for the given member can be determined, for example, based on the consistency of the values of at least some of the parameters over time (e.g., their consistency over a rolling average for a given time period, such as a ten-day rolling average). In some cases, the consistency of the values can be measured against reference parameters, for example: reference parameters that are measured from reference animals. Actual members of the animal population (other than the given member) or from another population can be used as reference animals. Historical data can also be used as reference. In some cases, the reference can be a theoretical reference of how a hypothetical reference animal should behave.

For the natural living score 440 calculation, the parameters that can be used for the calculation can include, for example, one or more of: (a) movement activity, including percentage of movement time for the given member within a certain time period (for example: the given member was on the move for 20% of the time within a given day or the given animal had a certain amount of high activity movement withing a given time period), (b) feeding activity, including percentage of feeding time for the given member within a certain time period (for example: the given member was feeding 25% of the time within a given day), (c) social activity, including percentage of social behavior time (e.g., time when the given member is interacting with another animal) for the given member within a certain time period (for example: the given member was engaged in social interaction for 10% of the time within a given day), or (d) schedule activity, changes in the schedule of the given member with respect to historical schedules (for example: if four feedings a day are the norm and less or more than that is taken on a given day).

The natural living score 440 calculation can be based on the values of these parameters and/or changes in the values of these monitored parameters over time. The natural living score 440 for the given member can be determined, for example, based on the consistency of the values of at least some of the parameters over time (e.g., the consistency of percentage of movement time during daytime over a rolling average for a given time period, such as a ten-day rolling average). In some cases, the consistency of the values can be measured against reference parameters, for example: reference parameters that are measured from reference animals.

Actual members of the animal population (other than the given member) or from another population can be used as reference animals. Historical data can also be used as reference. In some cases, the reference can be a theoretical reference of how a hypothetical reference animal should behave.

It is to be noted that in some cases, the determination of the natural living score 440 and/or of the affectivity/happiness score 430 of the respective member is also based on one or more environmental parameters, indicative of the state of the environment.

Non-limiting examples of such environmental parameters include weather conditions in the area of the animal, geographical location of the animal, ambient temperature around the animal, etc. that can affect the calculation of the natural living score 440 and/or of the affectivity/happiness score 430. For example: on cold days an animal is expected to stay inside and thus have less movement and less social interaction. Thus, system 200 will take the ambient temperature into consideration when determining the natural living score 440 and/or of the affectivity/happiness score 430. A low level of movement on a cold day could be given low weight for example with respect to the weight given to low level of movement on a warmer day.

It is to be noted that the environmental parameters can include one or more general environmental parameters that are not associated with a specific member of the animal population, and/or one or more member-specific environmental parameters that are associated with a specific member of the animal population. In the latter case, the member-specific environmental parameter can be included in the record associated with the specific member of the animal population.

Upon calculation of at least one of the health score 420, the natural living score 440 or the affectivity/happiness score 430 for the members of the first group, Welfare determination system 500 calculates a welfare score of the animal population based on any one, or any combination of: (a) the health scores 420 calculated for the first group of members, (b) the natural living scores 440 calculated for a second group of members, or (c) the affectivity/happiness scores 430 calculated for a third group of members (block 630).

In some cases, the welfare score can be a summation of averages of the health scores 420, the natural living scores 440, and the affectivity/happiness scores 430. In some cases, different weights can be assigned to each of the average scores, based on various considerations (e.g., based a level of credibility of the scores used to calculate the respective average, based on a variability of the scores used to calculate the respective average, etc.). In some cases, the welfare score can be normalized to a value between 0-100.

In some cases, the first group, the second group and the third group are identical and the calculation are made using the scores of all the members of the groups. In other cases, the calculation of the welfare score takes into account natural living scores 440 and/or affectivity/happiness scores 430 that have been calculated only for healthy members of the first group, e.g., members having health scores 420 above a threshold.

It is to be noted that in some cases the welfare score for the animal population, or any sub-group thereof, is calculated based on a variation between, or within, the individual scores (e.g., health scores 420, affectivity/happiness scores 430 and natural living scores 440) calculated for the members of the animal population, or the sub-group thereof.

A non-limiting example for the effect of variance within the individual affectivity/happiness scores 430 of the first group of the members, or variables used in its calculation, is that where a variation below one or more threshold ranges (e.g., for cows, one or more of: rumination variability below a range of 16-20% and/or for rumination times—variability below a threshold of 20-30 minutes and/or for heavy breath- ing—a variability in the levels of breathing below a range of 15-20%, etc.) is considered good (and thus this will not adversely affect the overall welfare score of the animal population), and a variation of more than one or more threshold ranges (e.g., for cows, one or more of: rumination variability above a range of 16-20% and/or for rumination times—variability above a threshold of 20-30 minutes and/ or for heavy breathing—a variability in the levels of breath- ing above a range of 15-20%, etc.) will result in the welfare score being reduced. It is to be noted that in this example reference is made to one or more threshold ranges, however this is by no means limiting, and the variations can be compared with one or more sliding scale calculated based on historical values of the affectivity/happiness scores 430 of the first group of the members, or variables used in its calculation.

It is to be noted that all the calculations mentioned can be optionally completed in real-time or near-real time, e.g., in very short intervals of times, close to instantaneous, or within up to a few seconds. Alternatively, the calculations may take minutes or more to complete.

Figure 10A:
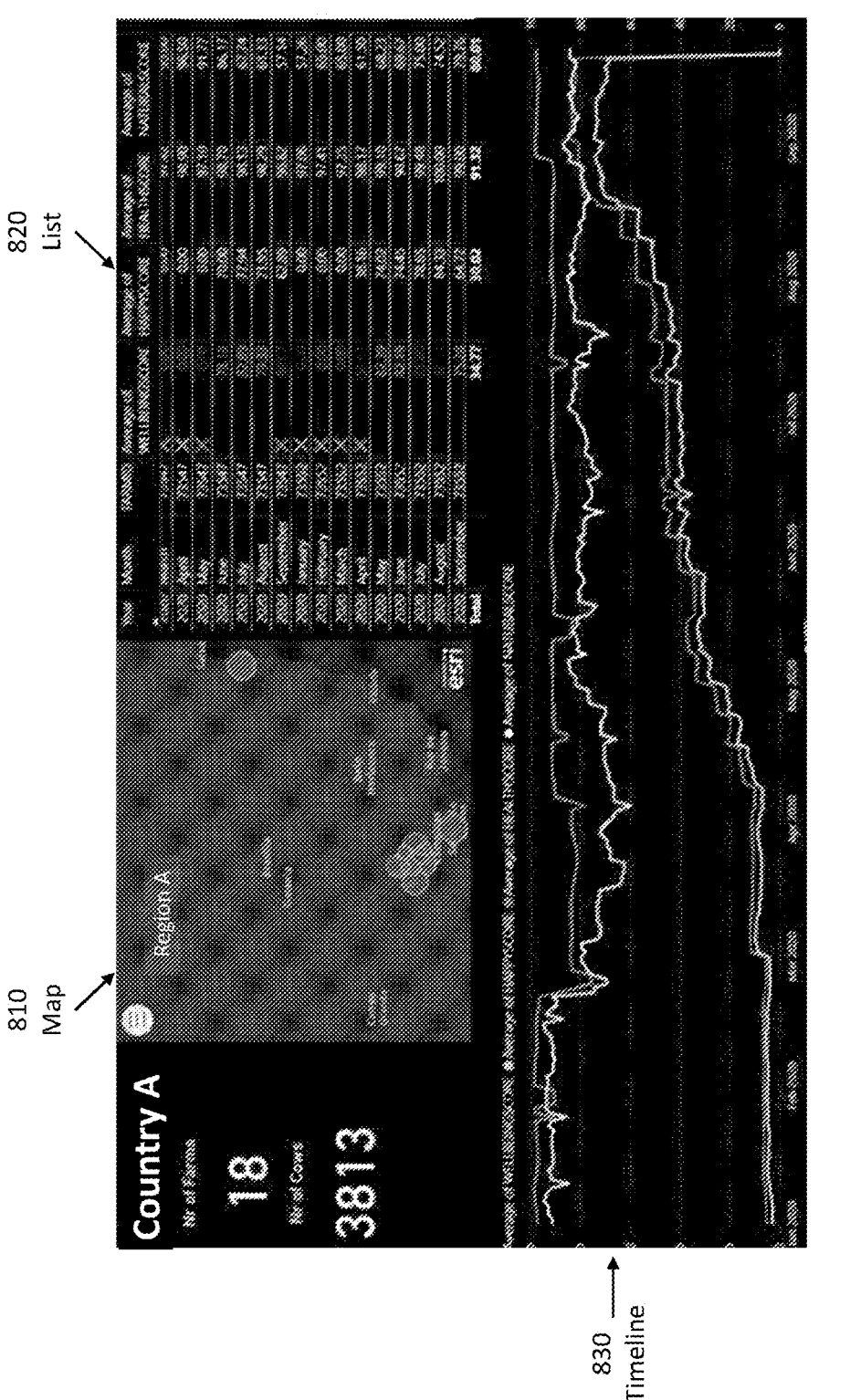
FIG. 10A is an illustration of one example of a Graphical User Interface (GUI) for a welfare determination system, in accordance with the presently disclosed subject matter.
Figure 10B:
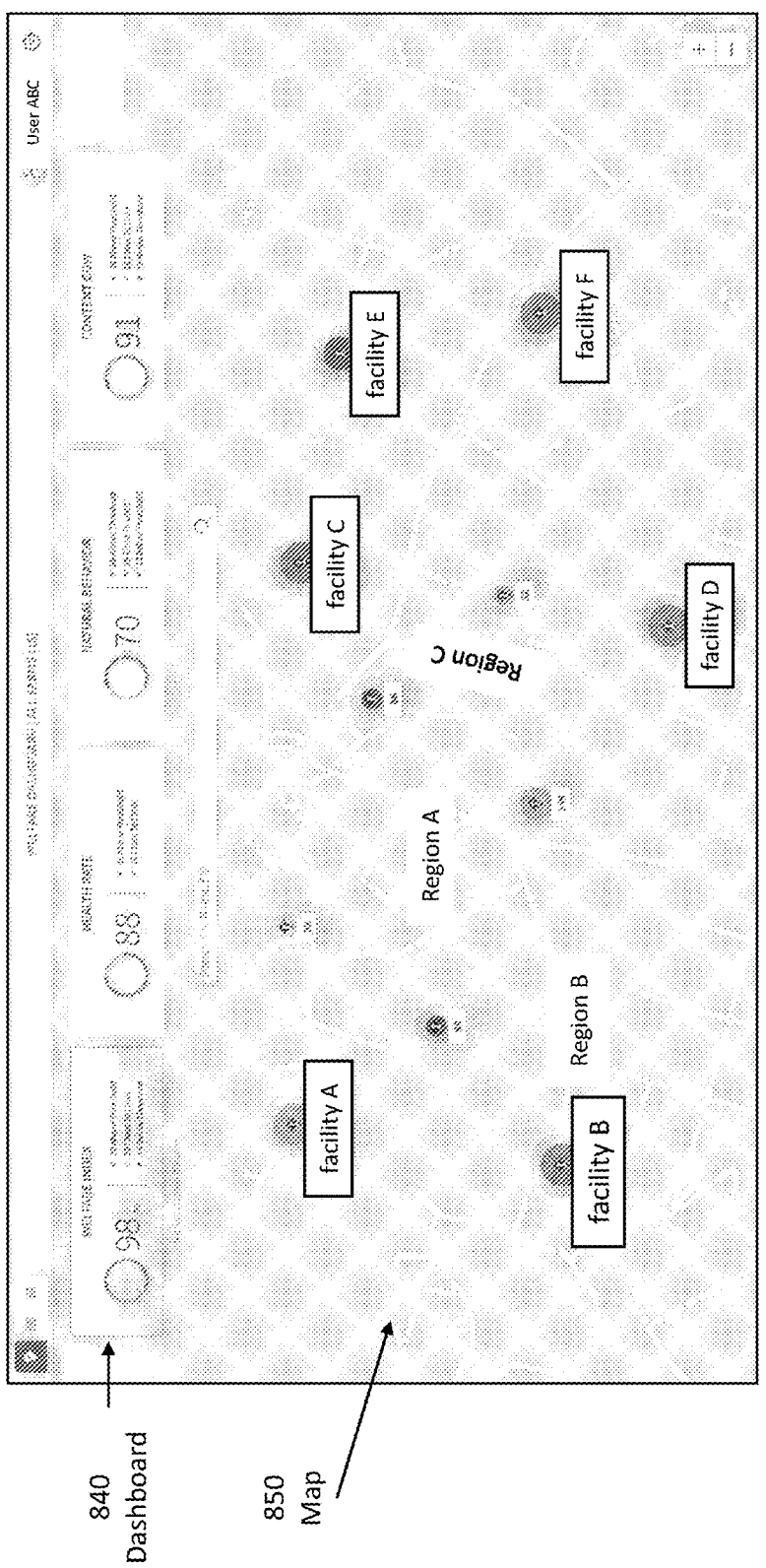
FIG. 10B is an illustration of another example of a GUI for a welfare determination system, in accordance with the presently disclosed subject matter.

In some cases, the calculated welfare scores for the animal population, or any sub-group thereof, can be presented to a user of system 200 utilizing a Graphical User Interface (GUI). A non-limiting illustration of examples of possible GUI screen used by system 200 are depicted in FIGS. 10A and 10B. The GUI can present current (and optionally real-time, or near real-time) and/or historical welfare KPI scores, including graphs and reports based on these current and/or historical welfare KPI scores.

Looking at FIG. 10A, there is shown a non-limiting GUI example, including: a map 810 GUI component, a list 820 GUI component and a timeline 830 GUI component. The map 810 displays one or more facilities (for example: farms) having animal populations that are monitored by Welfare determination system 500. The list 820 displays information about the facilities welfare KPI scores within a given timeframe (e.g., a calendric month, year, etc.) in a tabular format. The columns of list 820 include data about each facility within the given timeframe (e.g., average welfare KPI score, average health score 420, average affectivity/ happiness score 430, average natural living score 440, etc.) These components interrelate—when a user of system 500 choses one or more facilities using map 810 or list 820, the welfare KPI scores, the health scores 420, the affectivity/ happiness scores 430 and the natural living scores 440 for the chosen facilities over the given timeframe are presented within timeline 830. In addition, the GUI can present the user with historical trends of the calculated welfare KPI scores within the timeline 830 GUI component. The user of Welfare determination system 500 can use the GUI to generate a presentation of the calculated welfare scores in various timelines and/or regions. The GUI can present the data of a single group or of a number of groups in a comparative way. The one or more groups presented can be associated with one or more facilities so that the GUI can present welfare KPI scores for specific facilities or for groups of facilities. For example: the GUI can present a number of graphs (within timeline 830 GUI component) of the welfare KPI scores for the last year for all facilities in a number of geographical locations selected from map 810, thus giving the user of Welfare determination system 500 a tool to easily compare between the welfare KPI scores in different geographical locations.

Looking at FIG. 10B, there is shown another non-limiting GUI example, this example is a dashboard style GUI, including: map 850 GUI component and one or more dashboard 840 GUI components. The dashboard 840 GUI components can display different colors to indicate of the relative welfare KPI scores of animals in one or more locations, as chosen interactively by the user of system 500 from map 850 GUI component. For example: the number of animals with a welfare KPI score above a given threshold is marked green, the number of animals with a welfare KPI score within the given threshold is marked yellow and the number of animals with a welfare KPI score below the given threshold is marked red. Additional dashboard 840 GUI elements can be similarly color-coded to display the infor- mation for the health scores 420, the affectivity/happiness scores 430 and the natural living scores 440 for the animals in the chosen locations. In addition, the symbols for the facilities on the map can be similarly color coded. For example, facilities having a welfare KPI score below the given threshold can be marked red, facilities having a welfare KPI score above the given threshold can be marked green and facilities having a welfare KPI score within the given threshold can be marked yellow.

After calculating the welfare score, Welfare determination system 500 can be optionally configured to suggest an action to be taken on the animal population based on the welfare score (block 640). The action can be taken on a given member of the animal population, on a given group of members of the animal population (e.g., members of the animal population that are located in a certain location, such as a farm), or on the entire animal population.

The action can be, for example, a recommendation to the animal caregivers to change the human-animal relationship or to change the living environment and/or conditions of the animal/s. The recommendation can additionally, or alterna- tively, be to a regulator (such as a governmental organiza- tion) to perform actions in case the animal welfare is insufficient (noting that in some cases, the regulator can be provided with information on the welfare scores of the animal population/s under its supervision on a periodical or continuous manner, thereby enabling enforcing animal wel- fare requirements in a reliable, objective, repeatable and non-biased manner). The recommendation can additionally, or alternatively, be to a financial institution to make sure obligations of the animal caregiver to the financial institu- tion are met. The recommendation can additionally, or alternatively, be to retail chains, milk processors, or meat processors, to prefer purchasing products originating from one animal population over other animal populations (based on animal welfare scores calculated for a plurality of animal populations, or for a plurality of groups of animals from a single animal population). The recommendation can addi- tionally, or alternatively, be to veterinarians to proactively act upon identifying a need based on the animal welfare.

In some cases, the action can be executed automatically by an automated treatment system that is able to change the treatment given to the animal/s, upon receiving the sug- gested action from Welfare determination system 500.

It is to be noted that the action can be any action that influences one or more members of the animal population. For example: administering a treatment (vaccinating non- infected members of the animal population, providing anti- biotics, antiviral drugs, painkillers, anti-inflammatory drugs, general health boosters like vitamins and hormones like steroids, etc.) to one or more members of the animal population changing the environmental temperature that one or more members of the animal population are exposed to, changing the feeding parameters of one or more members of the animal population, changing a schedule or routine of one or more members of the animal population, changing sleeping parameters of one or more members of the animal population, separating one or more members of the animal population from the remaining members of the animal population, improving feed quality and availability to one or more members of the animal population, lowering house, bunk or both stocking rates, improving the housing/shelter conditions for one or more members of the animal population (e.g., by changing the environmental conditions control, bedding surface, walking routines, etc.), updating the Standard Operating Procedures (SOP) on a farm for better meeting the animal population's need, identifying outbreaks on time and acting accordingly, etc.

The action can be suggested also based on the health scores 420 and/or on the affectivity/happiness scores 430 and/or on the natural living scores 440 of the members of the animal population or a sub-group thereof.

The actions can be suggested based on determination of potential causes for a lower than desired welfare score, e.g., using rules that correlate potential causes to the welfare score and/or components thereof (the health scores 420 and/or on the affectivity/happiness scores 430 and/or on the natural living scores 440 of the members of the animal population or a sub-group thereof). As can be appreciated, correlations exist between certain potential causes (feed issues, bedding, social pressure, ambient temperature, production pressure) and lower welfare scores (or lower health scores 420 and/or affectivity/happiness scores 430 and/or natural living scores 440). Accordingly, Welfare determination system 500 can advise the animal care giver, based on these scores, to take one or more actions, along with a reasoning for providing such advice.

The potential causes can be determined by correlating behaviors of members of the animal population to circumstances or conditions (e.g., environmental conditions, operational conditions, human-relationship conditions, etc.) that impact one of the scores (the health scores 420 and/or on the affectivity/happiness scores 430 and/or on the natural living scores 440) described herein. For example, potential causes for increased variability of rumination and eating of members of the animal population can be a nutrition or feed issue, a bedding problem or social pressure the members of the animal population are suffering from. These causes can be correlated to the welfare scores Similarly, plausible causes for heavy breathing and enhanced variability of rumination and eating of members of the animal population can be an ambient temperature that is too high or an illness the members of the animal population are suffering from.

Attention is drawn to a non-limiting example of using the welfare KPIs in addition to the welfare score for suggesting an action: when (a) the welfare score of an animal population is lower than a first threshold, (b) a health score 420 for the animal population is lower than a second threshold, and (c) a natural living score 440 for the animal population is lower than a third threshold, the Welfare determination system 500 can suggest an action of an infectious disease inspection of the animal population. Alternatively, if only one, or two, of the welfare score, the health score 420 or the natural living score 440 are below a threshold, the Welfare determination system 500 can suggest another action—such as effectuating treatment for a potentially infectious disease.

In some cases, the action is suggested upon the welfare KPI scores being below a welfare threshold. The welfare threshold can be determined based on statistical analysis of historical welfare KPI scores (for example: using box plots, regression analysis, etc.). The historical welfare KPI scores can be used to identify trends within and/or between animal populations. The determination of the welfare threshold can be performed for one or more facilities (e.g., farms, etc.), geographical locations (e.g., territories, countries, etc.), etc.

It is to be noted that in some cases, different locations/territories have different regulatory and/or environmental conditions. Thus, an adjustable welfare threshold can take into consideration local regulation, local climate, local animal needs, local historical welfare scores, and other relevant factors, which results in a more realistic and useful welfare threshold(s) that can be adopted by different local stakeholders at different locations/territories.

Figure 11:
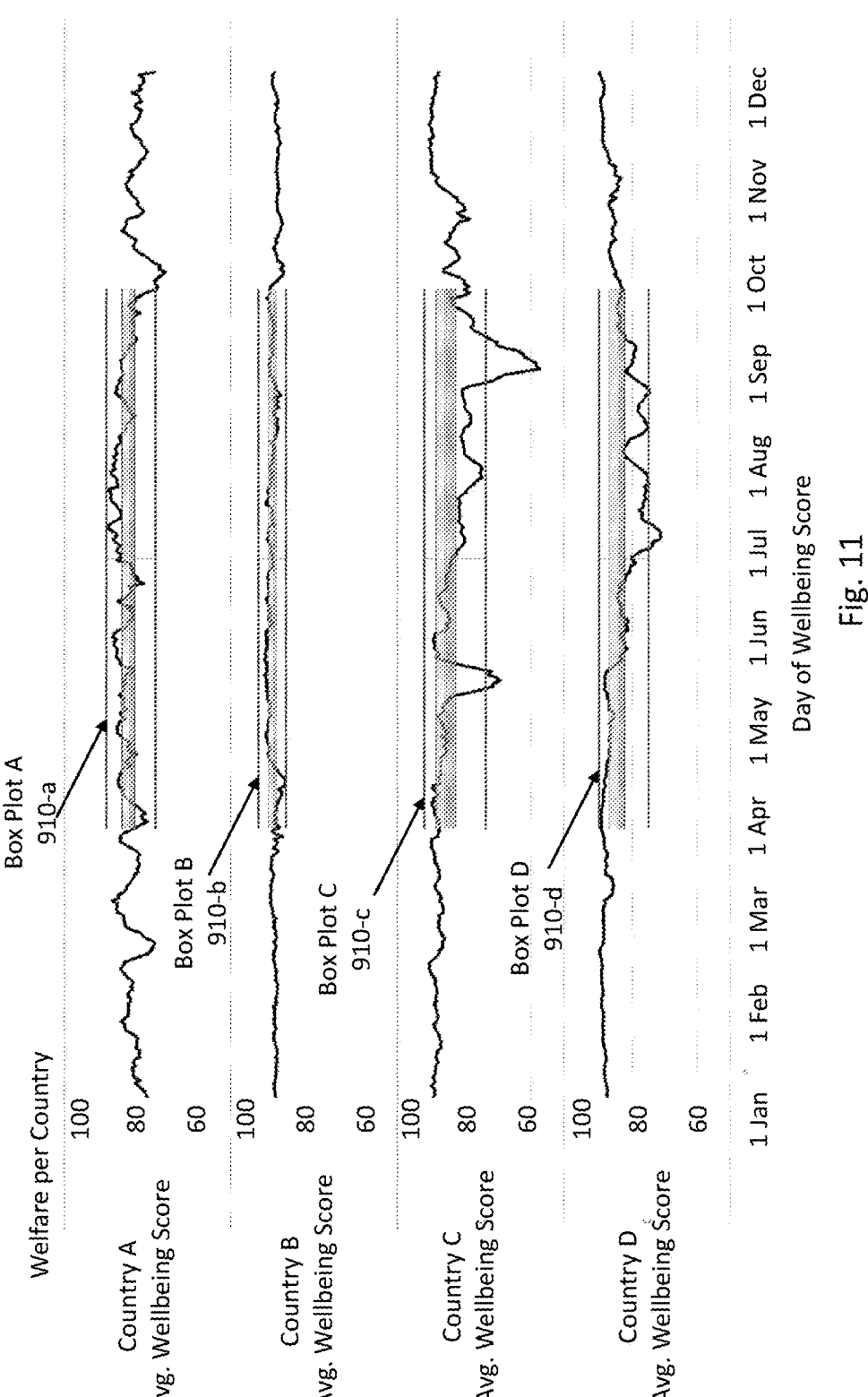
FIG. 11 is a schematic illustration of the determination of welfare thresholds in various countries, in accordance with the presently disclosed subject matter.

A non-limiting example is shown in FIG. 11, which shows graphs of average welfare scores as determined by Welfare determination system 500 over a time-period of a year for animal populations in four different countries. These graphs demonstrate the applicability of the welfare score model used by Welfare determination system 500 to various geographical areas, regions and countries having different environmental and seasonal conditions. The behavior of the welfare scores determined by Welfare determination system 500 matches known seasonal variations. For example: the dip in the welfare score in country C during May and September coincides with extreme heat conditions measured in that country. The welfare scores in the different countries are used to determine corresponding welfare thresholds. The welfare thresholds for a given geographical area, region or country can be determined statistically based on past welfare scores from that given geographical area, region or country. The statistical determination can be based on average, a mean, a box plot or any other statistical method. A non-limiting example of determining the welfare thresholds for various countries using a box plot (e.g., box plot A 910-*a*, box plot B 910-*b*, box plot C 910-*c*, box plot D 910-*d*, etc.) method is depicted in the graphs of FIG. 11—depicting welfare thresholds determined for four different countries during a corresponding given time frame. Box plot is a known statistical method for graphically depicting groups of numerical data through their quartiles. For example: box plot A 910-*a* has four vertical quartiles (colored white, light gray, dark gray and white). The first quartile, which is the lowest part of box plot A 910-*a*, holds the median of the lower half of the dataset. The threshold in this example is set to this first quartile—welfare scores that are above the first quartile are above the welfare threshold and welfare scores in the first quartile are below the welfare threshold. This method generated different welfare thresholds for different countries and can be used to determine different welfare thresholds for different time-periods within the same country. It can be appreciated that the welfare thresholds vary between the four countries.

It is to be noted that Welfare determination system 500 can set different thresholds for the different locations due to differences between the locations, such as: different animal types, different climate, different customs, different regulation and rules, different laws, different demands on the animals. Welfare determination system's 500 continuous and constant monitoring enables a user of Welfare determination system 500 (such as: an animal care giver) to set appropriate thresholds for his location. Each location can be, for example, a farm, a group of farms, a region, a territory, a country, etc.

It is to be noted that the welfare threshold can also change dynamically (e.g., according to weather) and/or periodically (e.g., seasonally). With reference to seasonal related changes, it is to be noted that analysis of historical welfare score enables deamination of periods of the year where the animal population's welfare scores are influenced from weather conditions, the season of year, or other local variable conditions. It can be readily appreciated that the seasonal change is geography dependent and in may vary between countries, or even between geographical areas within a country.

It is to be noted that Welfare determination system 500 can set different thresholds for the different locations due to differences between the locations, such as: different animal types, different climate, different customs, different regulation and rules, different laws, different demands on the animals. Welfare determination system's 500 continuous and constant monitoring enables a user of Welfare determination system 500 (such as: an animal care giver) to set appropriate thresholds for his location. Each location can be, for example, a farm, a group of farms, a region, a territory, a country, etc.

It is to be noted that the welfare threshold can also change dynamically (e.g., according to weather) and/or periodically (e.g., seasonally). With reference to seasonal related changes, it is to be noted that analysis of historical welfare KPI score enables deamination of periods of the year where the animal population's welfare KPI scores are influenced from weather conditions, the season of year, or other local variable conditions. It can be readily appreciated that the seasonal change is geography dependent and in may vary between countries, or even between geographical areas within a country.

Figure 12:
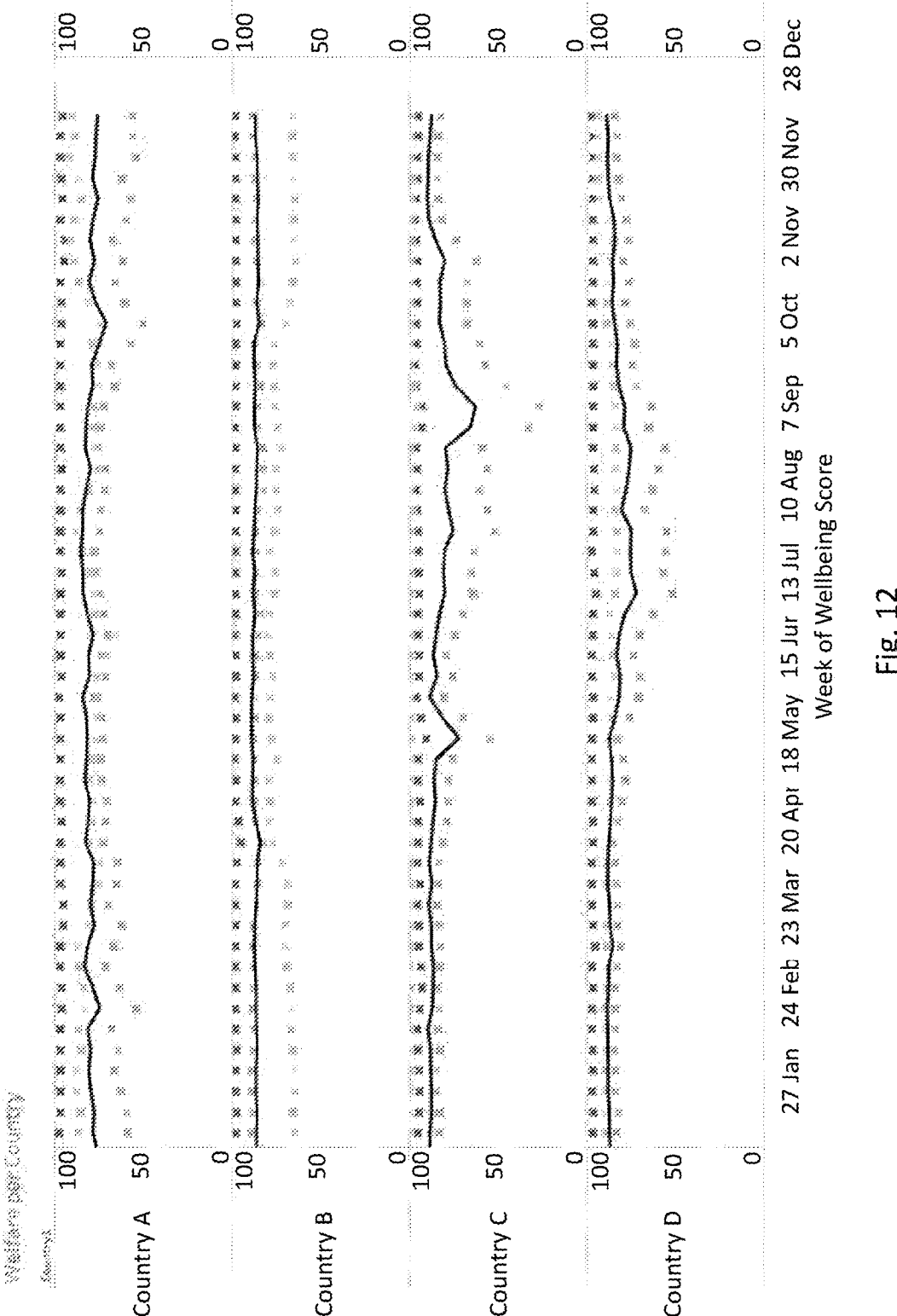
FIG. 12 is a schematic illustration of the effects of weather and seasons on welfare scores, in accordance with the presently disclosed subject matter.

A non-limiting example is shown if FIG. 12, in which data collected from four countries is shown. In "Country A", between January to March and October to December the animals are exposed to conditions that affect the affectivity/happiness score 430 and between April to August there are more issues affecting the natural living score 440. For example, this can be due to tropical climate in "Country A" and the impact of a wet versus dry seasons. In "Country B", between April to October, once animals are allowed into paddocks, the natural living score 440 is improved due to the better conditions compared with the over stocking conditions when housed. The affectivity/happiness score 430 in the same period are osculating more due to feed quality and climate conditions. Further, in "Country C" and "Country D" the graphs depict the impact of extreme conditions: extreme heat stress in May and September pulled the overall welfare KPI score down although the animal environment was not changed. These weather and seasonal effects may be missed by a human auditor, that would clearly not be able to notice smaller and subtler impacts of varying climates, conditions, and environments that can be identified using the Welfare determination system 500.

Welfare determination system's 500 welfare KPI scores have been validated against human auditors' welfare KPI scores and the welfare KPI scores generated by system 500 have been found to be valid and useful. For example, the welfare scores determined by the Welfare determination system 500 showed good correlation with welfare scores on the same animals as determined by a human audit. In addition, the Welfare determination system 500 also provided additional insight, more accurate insight, and more complete insight than the human led audits. This provides examples of the improvement of the current disclosure over the prior art.

In a number of exemplary studies, the welfare KPI scores generated by Welfare determination system 500 have been blindly compared with human auditing on representative farm operations. One example involved a population of grazing cows. The human auditor gave a low overall welfare KPI score due to the observation of missing facilities and poor feeding conditions. By contrast, system's 500 welfare KPI scores for the same grazing cows was higher. To prove that the Welfare determination system's 500 scores were more accurate, a number of indicators have been examined: lack of illness signs, no diseases for that group of cows, lameness was not observed among these cows, constant feed behavior; additionally the Somatic Cell Count (SCC) of the milk of these cows was tested and found to be at constant and appropriate levels, consistent yield levels, all are indicators that the cow's welfare was not low—as indicated by the human auditor. Indeed, because the cows were low yielding cows naturally, they were able to maintain good welfare despite the external conditions judged to be detrimental to welfare by the human auditor. The human auditor was not able to directly measure the cow's welfare and judge if these external conditions were adversely impacting the welfare. By contrast, the more direct measurement of the animal's welfare, using the Welfare determination system 500, was able to achieve this. Thus, this is one example of the Welfare determination system 500 described herein providing a more accurate determination of welfare of the cows on the farm.

Another example included a population of high yielding cows that were fed on a Total Mixed Ration (TMR) diet. The human auditor found missing housing facilities, problematic stocking rates and cows that were dirty and thus gave a low welfare KPI score. Welfare determination system's 500 welfare KPI scores for the same high yielding cows was relatively high since Welfare determination system 500 took into consideration the consistent TMR, the sufficient bunk space, the efficient cooling solution provided to the cows and the acceptable health score 420 result. As animals' responses to enforced conditions is multifactorial it is hard for a human auditor to grasp without more frequent or continuous monitoring. Human auditors usually notice only the external drop in performance of the animal—when it is usually too late to repair the situation. This is another example of the human auditor relying on external observations without having the benefit of the direct and continuous measurement of the cow's welfare as the currently disclosed Welfare determination system 500 employs.

Figure 13:
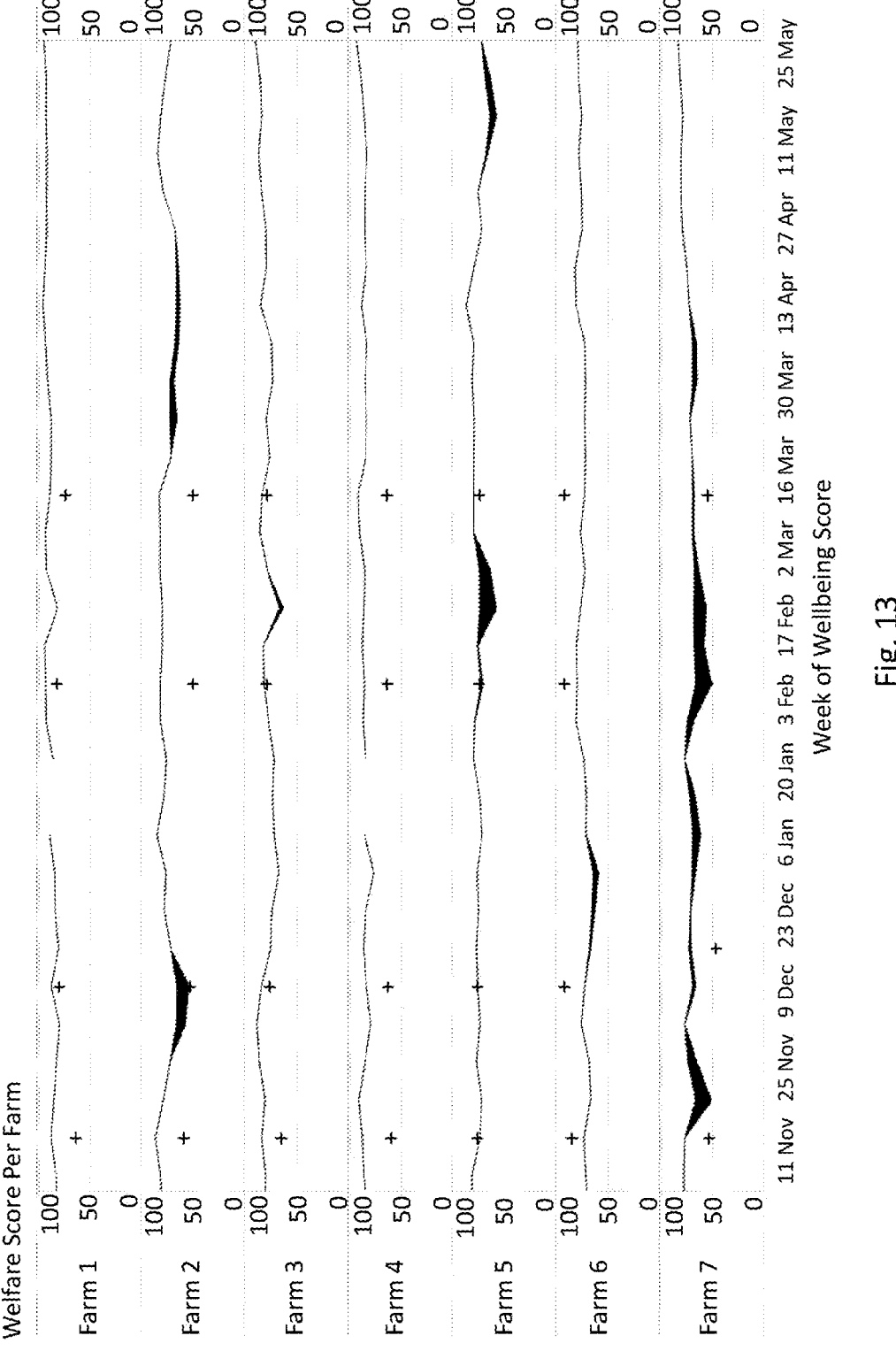
FIG. 13 is a schematic illustration of an exemplary comparison of human auditors determined welfare scores and welfare KPI scores determined by the system in various facilities, in accordance with the presently disclosed subject matter; and, FIG. 14 is a schematic illustration of an example of the consistency between human auditors determined welfare scores and welfare KPI scores determined by the system, in accordance with the presently disclosed subject matter.

FIG. 13 depicts a number of non-limiting examples of welfare scores as determined by human auditors (marked by +) and Welfare determination system's 500 welfare scores (marked by solid lines) at parallel timeframes for a number of given facilities. The areas where the welfare score lines are thicker are associated with the time where the welfare scores were more frequently dropping below the set welfare threshold. It is to be noted that the data in FIG. 13 is actual data from usage of Welfare determination system 500 monitoring these facilities, thereby validating the welfare KPI scores generated by system 500.

In some cases, a human auditor may determine a welfare score for a given animal population that is lower than a welfare KPI score determined by Welfare determination system 500 for the same given animal population. This can occur because the data and analysis available to the human auditor (e.g., production levels, visual inspections of the animal's environment, etc.) is inferior to Welfare determination system's 500 data that can be acquired through continuous monitoring and analysis of the behaviors of members of the animal population (e.g., feeding levels, rumination times, activity and energy levels, etc.) to accurately determine their welfare KPI scores. A higher score given by Welfare determination system 500 can also be a result of comparing the measured behavior to a rolling baseline behavior and adjusting the welfare KPI score for the impact of extreme events or slowly deteriorating conditions that are not easily judged by infrequent human audits. Without the ability to compare to a rolling baseline and adjusting for the impact of events such as weather (for example: seasonal weather, extreme weather, etc.), slowly changing conditions (for example: a slow decline is animals' facilities), or subtle changes over time, the human auditor may determine a lower welfare score than the one determined by Welfare determination system 500 for the same animal population under the same conditions. In a real-life example, a farm which received a medium-low welfare score from a human auditor due to unclean animal living quarters, low food supplies and low production levels, received a high welfare KPI score from Welfare determination system 500 which was in-synch with the animals' actual welfare—the animals had low pressure due to the low productivity expectations and the living quarters actually gave the animals an opportunity to rest and to cool themselves.

A non-limiting example of where the audited score is above the welfare KPI scores calculated by Welfare determination system 500 is when environmental conditions change (such as: extreme weather conditions) but the animal living conditions haven't changed. The human auditor score is biased towards the living conditions viewed by the auditor, and thus gives a high auditing score. Welfare determination system's 500 monitoring (that is optionally continuous) senses the effects of the change in the environmental conditions on the animals and thus gives a lower welfare KPI score that is more aligned with the reality of the animals.

Another non-limiting example of where the audited score is above the welfare KPI scores calculated by Welfare determination system 500 is when the animals are under high physiological pressure (e.g., high production pressure, high workload pressure, etc.). A human auditor is impressed with the yield of the animals and by the farm's physical conditions, but system 500 continuously monitoring of the animals' behaviour detects the high pressure and the animals' reaction to that pressure that results in a low welfare KPI score.

The areas of disagreement between the human auditing welfare scores and system's 500 welfare KPI scores that are based on automatic, and optionally continuous, monitoring, derive from Welfare determination system 500 taking into account also the historical trends whereas human auditing is based on an evaluation performed during the time of the audit only. There is no human bias in Welfare determination system's 500 welfare KPI score determination—no personal impression, no repeatability problems and no auditing proficiency. Welfare determination system 500 judges the welfare conditions from the animal's physiological signals and not by human interpretation. Welfare determination system 500 can provide higher sensitivity for chronic states such as overstocking, or extreme conditions such as heavy heat stress. Welfare determination system 500 can provide higher specificity in situations where animals can manage the enforced environment due to less depended production or conditions.

Figure 14:
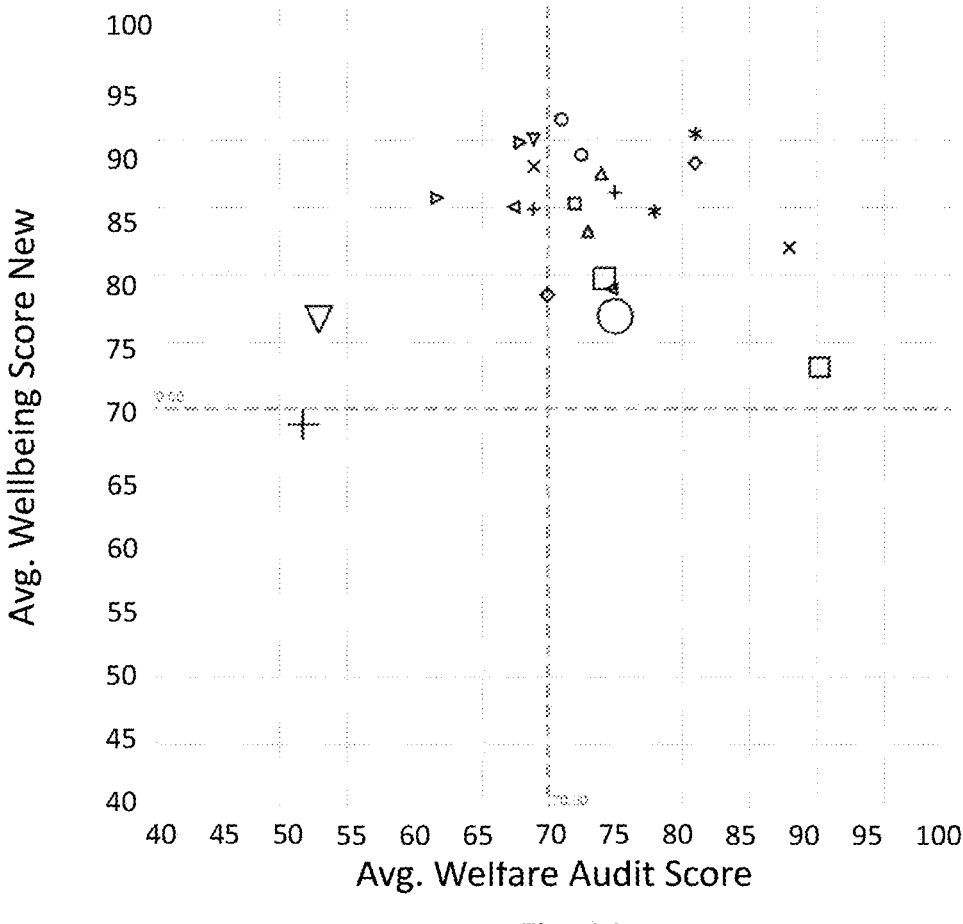

FIG. 14 depicts the consistency between human auditors determined welfare scores and welfare KPI scores determined by Welfare determination system 500. The upper right part and the lower left part of the graph in FIG. 14 (where most of the validation measurements are found) is where there is general agreement between the human auditor's welfare scores and the welfare KPI scores determined by Welfare determination system 500. The size of the icon in the graph is associated with the welfare KPI scores that are more frequently dropping below the welfare threshold.

Human auditing is limited due to inconsistencies, reputability and precision problems. Welfare determination system 500 mitigates these limitations by providing an accurate and optionally continuous welfare KPI score.

These comparative studies have found that as result of the optionally ²⁴⁄₇ coverage of Welfare determination system 500 and the individual monitoring performance of the calculated welfare KPI scores, system 500 delivers a more truthful representation of the reality of the animal population. For example, the Welfare determination system 500 is better equipped to deal with scenarios like: uneven operational consistency, extreme weather conditions, oscillating morbidity, and more. The studies have found that production demand has a significant impact on the welfare reflection, i.e., lower production makes harder conditions more tolerated. Based on proven insights, the calculated monitoring welfare score provides an objective (non-human interpreted) view of the animal population condition.

It is to be noted, with reference to FIGS. 3, 5 and 8, that some of the blocks can be integrated into a consolidated block or can be broken down to a few blocks and/or other blocks may be added. It is to be further noted that some of the blocks are optional. It should be also noted that whilst the flow diagram is described also with reference to the system elements that realizes them, this is by no means binding, and the blocks can be performed by elements other than those described herein.

It is to be understood that the presently disclosed subject matter is not limited in its application to the details set forth in the description contained herein or illustrated in the drawings. The presently disclosed subject matter is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based may readily be utilized as a basis for designing other structures, methods, and systems for carrying out the several purposes of the present presently disclosed subject matter.

It will also be understood that the system according to the presently disclosed subject matter can be implemented, at least partly, as a suitably programmed computer. Likewise, the presently disclosed subject matter contemplates a computer program being readable by a computer for executing the disclosed method. The presently disclosed subject matter further contemplates a machine-readable memory tangibly embodying a program of instructions executable by the machine for executing the disclosed method.

What is claimed is:

1. A system for evaluating the level of harassment of flying insects on a plurality of animals located at a given area, the system comprising a processing circuitry configured to:

obtain one or more ear movement patterns caused by harassment or irritation of flying insects, each ear movement pattern being associated with at least one ear of each of two or more animals of said animals, wherein the ear movement patterns are determined by analyzing sensor data acquired by at least one sensor associated with the respective ear of each of the two or more animals, and wherein each ear movement pattern comprises corresponding ear movement characteristics;

for at least a portion of the one or more ear movement patterns, determine whether their respective ear movement characteristics meet a predefined rule;

determine whether a number of ear movement patterns, whose ear movement characteristics met the predefined rule, meets an action requirement rule; and, in response to the action requirement rule being met, perform an action configured to reduce the harassment level within said given area.

2. The system according to claim 1, wherein each of the one or more ear movement patterns is associated with its own characteristics.

3. The system according to claim 1, wherein the one or more ear movement patterns are associated with characteristics common to all ear movement patterns.

4. The system according to claim 1, wherein the action requirement rule is one of: (a) the number of ear movement patterns whose characteristics met the predefined rule is above a first harassment threshold, (b) a percentage of the number of ear movement patterns whose characteristics met the predefined rule from a number of the plurality of animals is above a second harassment threshold.

5. The system according to claim 1, wherein the action includes at least one of: installing flying insects' papers, installing flying insects' traps, installing pesticide-releasing flying insects' strips, using repellent flying insects' sprays, using flying insects' predators, or any combination thereof.

6. The system according to claim 1, wherein the action is directed to attend to one or more health conditions.

7. The system according to claim 1, wherein said at least one sensor is an accelerometer coupled to the said at least one ear.

8. The system according to claim 7, wherein said accelerometer is part of a respective ear tag attached to the at least one ear of each of two or more animals of said animals.

9. A method for evaluating the level of harassment of flying insects on a plurality of animals located at a given area, the method comprising:

obtaining one or more ear movement patterns caused by harassment or irritation of flying insects, each ear movement pattern being associated with at least one ear of each of two or more animals of said animals, wherein the ear movement patterns are determined by analyzing sensor data acquired by at least one sensor associated with the respective ear of each of the two or more animals, and wherein each ear movement pattern comprises corresponding ear movement characteristics;

for at least a portion of the one or more ear movement patterns, determining whether their respective ear movement characteristics meet a predefined rule;

determining whether a number of ear movement patterns, whose ear movement characteristics met the predefined rule, meets an action requirement rule; and, in response to the action requirement rule being met, perform an action configured to reduce the harassment level within said given area.

10. The method according to claim 9, wherein the one or more ear movement patterns are associated with characteristics common to all ear movement patterns.

11. The method according to claim 9, wherein each of the one or more ear movement patterns is associated with its own characteristics.

12. The method according to claim 9, wherein the action requirement rule is one of: (a) the number of ear movement patterns whose characteristics met the predefined rule is above a first harassment threshold, (b) a percentage of the number of ear movement patterns whose characteristics met the predefined rule from a number of the plurality of animals is above a second harassment threshold.

13. The method according to claim 9, wherein the action includes at least one of: installing flying insects' papers, installing flying insects' traps, installing pesticide-releasing flying insects' strips, using repellent flying insects' sprays, using flying insects' predators, or any combination thereof.

14. The method according to claim 9, wherein said at least one sensor is an accelerometer coupled to said at least one ear.

15. The method according to claim 14, wherein said accelerometer is part of a respective ear tag attached to the at least one ear of each of two or more animals of said animals.

16. A non-transitory computer readable storage medium having computer readable program code embodied therewith, the computer readable program code, executable by at least one processor to perform a method for evaluating the level of harassment of flying insects on a plurality of animals located at a given area, the harassment evaluation comprising one or more components, the method comprising:

obtaining one or more ear movement patterns caused by harassment or irritation of flying insects, each ear movement pattern being associated with at least one ear of each of two or more animals of said animals, wherein the ear movement patterns are determined by analyzing sensor d acquired by at least one sensor associated with the respective ear of each of the two or more animals, and wherein each ear movement pattern comprises corresponding ear movement characteristics;

for at least a portion of the one or more ear movement patterns, determining whether their respective ear movement characteristics meet a predefined rule;

determining whether a number of ear movement patterns, whose ear movement characteristics met the predefined rule, meets an action requirement rule; and, in response to the action requirement rule being met, perform an action configured to reduce the harassment level within said given area.

\* \* \* \* \*